United States Patent
Strommer et al.

(10) Patent No.: US 8,131,344 B2
(45) Date of Patent: *Mar. 6, 2012

(54) METHOD AND SYSTEM FOR REGISTERING A MEDICAL SITUATION ASSOCIATED WITH A FIRST COORDINATE SYSTEM, IN A SECOND COORDINATE SYSTEM USING AN MPS SYSTEM

(75) Inventors: Gera Strommer, Haifa (IL); Uzi Eichler, Haifa (IL)

(73) Assignee: MediGuide, Ltd., Haifa (IL)

( * ) Notice: Subject to any disclaimer, the term of this patent is extended or adjusted under 35 U.S.C. 154(b) by 489 days.

This patent is subject to a terminal disclaimer.

(21) Appl. No.: 12/366,900

(22) Filed: Feb. 6, 2009

(65) Prior Publication Data

US 2009/0137901 A1    May 28, 2009

Related U.S. Application Data

(63) Continuation of application No. 10/458,332, filed on Jun. 9, 2003, now Pat. No. 7,505,809, which is a continuation of application No. 10/341,535, filed on Jan. 13, 2003, now abandoned.

(51) Int. Cl.
*A61B 5/00* (2006.01)
(52) U.S. Cl. ........ 600/424; 600/411; 600/427; 600/428; 600/439; 600/474; 600/476; 702/150
(58) Field of Classification Search .......... 600/407, 600/411, 427, 428, 437, 439, 474, 476; 324/207.11, 324/207.13, 207.22; 128/920, 922; 702/150–153
See application file for complete search history.

(56) References Cited

U.S. PATENT DOCUMENTS

| | | | |
|---|---|---|---|
| 3,974,826 A | 8/1976 | Eggleton et al. |
| 3,990,296 A | 11/1976 | Erikson |
| 4,262,306 A | 4/1981 | Renner et al. |
| 4,737,794 A | 4/1988 | Jones |
| 5,016,642 A | 5/1991 | Dukes et al. |
| 5,152,290 A | 10/1992 | Freeland |
| 5,159,931 A | 11/1992 | Pini |
| 5,398,691 A | 3/1995 | Martin et al. |
| 5,453,686 A | 9/1995 | Anderson |
| 5,529,070 A | 6/1996 | Augustine et al. |
| 5,540,229 A | 7/1996 | Collet-Billon et al. |
| 5,588,432 A | 12/1996 | Crowley |
| 5,662,111 A | 9/1997 | Cosman |
| 5,690,113 A | 11/1997 | Sliwa, Jr. et al. |
| 5,744,953 A | 4/1998 | Hansen |
| 5,787,889 A | 8/1998 | Edwards et al. |

(Continued)

FOREIGN PATENT DOCUMENTS

EP    0930046 A2    7/1999

*Primary Examiner* — Ruth S Smith
(74) *Attorney, Agent, or Firm* — Dykema Gossett PLLC

(57) ABSTRACT

System for registering a first coordinate system with a second coordinate system, the system including a first medical positioning system for detecting a first position and orientation of the body of a patient, a second medical positioning system for detecting a second position and orientation of the body, and a registering module coupled with a medical intervention device and with the second medical positioning system, the first medical positioning system being associated with and coupled with an imager, the imager acquiring an image of the body, the registering module registering the first coordinate system with the second coordinate system, according to the first position and orientation and the second position and orientation.

20 Claims, 21 Drawing Sheets

U.S. PATENT DOCUMENTS

| | | |
|---|---|---|
| 5,806,521 A | 9/1998 | Morimoto et al. |
| 5,830,145 A | 11/1998 | Tenhoff |
| 5,846,200 A | 12/1998 | Schwartz |
| 5,899,860 A | 5/1999 | Pfeiffer et al. |
| 5,913,820 A | 6/1999 | Bladen et al. |
| 5,924,989 A | 7/1999 | Polz |
| 5,935,075 A | 8/1999 | Casscells |
| 5,949,491 A | 9/1999 | Callahan et al. |
| 5,954,647 A | 9/1999 | Bova et al. |
| 5,955,879 A | 9/1999 | Durdle et al. |
| 5,957,844 A | 9/1999 | Dekel et al. |
| 5,967,980 A | 10/1999 | Ferre et al. |
| 5,976,088 A | 11/1999 | Urbano et al. |
| 5,993,390 A | 11/1999 | Savord et al. |
| 5,994,690 A | 11/1999 | Kulharni et al. |
| 6,006,126 A | 12/1999 | Cosman |
| 6,134,003 A | 10/2000 | Tearney et al. |
| 6,175,669 B1 | 1/2001 | Colston et al. |
| 6,216,029 B1 | 4/2001 | Paltieli et al. |
| 6,233,476 B1 | 5/2001 | Strommer et al. |
| 6,246,898 B1 | 6/2001 | Vesely et al. |
| 6,314,310 B1 | 11/2001 | Ben-Haim et al. |
| 6,351,513 B1 | 2/2002 | Bani-Hashemi et al. |
| 6,390,982 B1 | 5/2002 | Bova et al. |
| 6,405,072 B1 | 6/2002 | Cosman |
| 6,421,551 B1 | 7/2002 | Kuth et al. |
| 6,454,766 B1 * | 9/2002 | Swanson et al. ............... 606/41 |
| 6,775,404 B1 | 8/2004 | Pagoulatos et al. |
| 6,898,454 B2 * | 5/2005 | Atalar et al. ................. 600/410 |
| 7,505,809 B2 * | 3/2009 | Strommer et al. ............ 600/424 |
| 7,881,767 B2 * | 2/2011 | Strommer et al. ............ 600/407 |
| 2002/0049375 A1 | 4/2002 | Strommer et al. |
| 2002/0193685 A1 | 12/2002 | Mate et al. |

* cited by examiner

METHOD AND SYSTEM FOR REGISTERING A MEDICAL SITUATION ASSOCIATED WITH A FIRST COORDINATE SYSTEM, IN A SECOND COORDINATE SYSTEM USING AN MPS SYSTEM

CROSS-REFERENCE TO RELATED APPLICATIONS

The present application is a continuation of U.S. application Ser. No. 10/458,332, filed on Jun. 9, 2003, now U.S. Pat. No. 7,505,809, which is a continuation of U.S. application Ser. No. 10/341,535, filed on Jan. 13, 2003, now abandoned.

FIELD OF THE DISCLOSED TECHNIQUE

The disclosed technique relates to medical devices in general, and to methods and systems for acquiring images of the body of a patient, in particular.

BACKGROUND OF THE DISCLOSED TECHNIQUE

A physician who performs an operation on the body of a patient, generally employs a real-time imaging system, in order to view the location and orientation of the medical intervention device (e.g., catheter, needle), within the body of the patient during the operation. Such real-time imaging systems are known in the art. These systems generally enable a display to display a representation of the medical intervention device superimposed on an image of the body of the patient.

U.S. Pat. No. 6,351,513 issued to Bani-Hashemi et al., and entitled "Fluoroscopy Based 3-D Neural Navigation Based on Co-Registration of Other Modalities with 3-D Angiography Reconstruction Data", is directed to a method for displaying a real-time 3-D reconstruction of a catheter within a 3-D angiography reconstruction of a vessel. The method includes the procedures of acquiring a 3-D angiography image of the arterial tree by a computed tomography device and registering the 3-D angiography image with a 2-D fluoroscopic image of a vessel, according to the structural similarities (i.e., anatomical landmarks).

The method further includes the procedures of determining the projecting lines of the catheter by using an X-ray apparatus, determining the location of the catheter, by intersecting the 3-D angiography image with the projecting lines and displaying a 3-D visualization of the 3-D reconstruction of the catheter within the 3-D angiography reconstruction of the vessel. The 3-D visualization of the catheter is updated as the catheter is moved.

U.S. Pat. No. 6,314,310 issued to Ben-Haim et al., and entitled "X-Ray Guided Surgical Location System with Extended Mapping Volume", is directed to a system for inserting a needle into a selected location of the vertebrae of a patient. The system includes a reference element, a plurality of magnetic field generator coils, a driver circuitry, a computer, a user interface control, a display, a fluoroscope and a computer tomography (CT) device. The reference element is in form of a plastic disc transparent to visible light and X-rays, which includes three equally spaced metal fiducial marks at the periphery thereof, a first position and orientation sensing device at the center thereof and another fiducial mark adjacent the first position and orientation sensing device. The needle includes a second position and orientation sensing device.

The magnetic field generator coils are placed on or adjacent to a bed on which the patient lies. The fluoroscope irradiates the patient from one side of the body of the patient. The computer controls multiple aspects of the system. The first position and orientation device and the second position and orientation device sends signals to the computer, respective of the time-varying magnetic fields generated by the magnetic field generator coils. The computer analyzes the signals to determine the six-dimensional position and orientation coordinates of the first position and orientation device and the second position and orientation device, relative to a common frame of reference defined by the magnetic field generator coils. The computer enables the display to display an image of the vertebrae, a representation of the first position and orientation device and the second position and orientation device and a representation of the needle and the fiducial marks. The location and the angular orientation of the reference element are determined by determining the two-dimensional coordinates of the representation of the fiducial marks. A scaling factor is determined for the images displayed on the display, by comparing the determined coordinates with the known positions of the fiducial marks.

While acquiring CT images of the body of the patient, the reference element is fixed to the body and remains fixed to the body in this position during the surgery. The CT images are registered with the X-ray images, by comparing the image-derived coordinates of the fiducial marks of the reference element, which appear in the CT images, with the image-derived coordinates of the fiducial marks in the X-ray images. The fiducial marks of the reference element and the fiducial marks in the X-ray images are visible marks. The three-dimensional CT images are rotated or scaled, in order to align the CT images with the X-ray images and the CT images are projected onto the plane of the X-ray images and superimposed on the X-ray images or displayed alongside the X-ray images.

U.S. Pat. No. 6,421,551 issued to Kuth et al., and entitled "Method for Registering Images of a Subject with a Magnetic Resonance System and Magnetic Resonance System for the Implementation of the Method", is directed to a system for readjusting the tomogram plane of an image of the body of a patient. The system includes a control console, a magnetic resonance system, a stereoscopic camera and a marking element. The control console includes a control unit, an image data generator and processor, a coordinate transformation unit, a readjustment unit and a tomogram selecting unit. The magnetic resonance system includes two pole shoes which are located opposite one another.

The control console is connected to the magnetic resonance system and to the stereoscopic camera. The marking element is composed of three reflective balls and is arranged at the patient in the region of the knee joint, in a first coordinate system. The stereoscopic camera acquires an image of the reflective balls and sends the respective position data to the control console. The coordinate transformation unit transforms the position data from the first coordinate system to a second coordinate system of the magnetic resonance system. When the relative movement of the patient is known, the readjustment unit readjusts the previously defined tomogram plane, such that it again lies relative to the marking element with respect to the knee joint, as it did in the preceding joint position.

One way to destroy tumors in a patient, and to prevent metastasis, is by subjecting the target tissue to radiation therapy. One type of radiation therapy is known as linear acceleration, whereby a beam of x-rays or electrons is directed at the target tissue from different directions. Each time the linear accelerator directs a beam towards the target tissue it also irradiates healthy tissue which surrounds the target tissue, along the path of the irradiation beam. Accordingly, such surrounding tissue is irradiated significantly less than the target tissue.

The linear accelerator is programmed to irradiate a specific volume which is generally similar to the shape of the target tissue. Accordingly, the portion of the body including the target tissue, has to be placed such that the target tissue is located within that specific volume. A conventional linear acceleration treatment includes a plurality of recurring procedures, usually over a period of several days or weeks. Each time, the portion of the body including the target tissue, has to be placed exactly as it was placed in the first treatment.

For this purpose, during the first radiation session, after locating the portion of the body which contains the target tissue at a location appropriate for irradiation, a plurality of non-hazardous laser beams, for example four beams, are directed from fixed locations, toward that portion of the body. These four points are marked by a permanent marker, such as a waterproof marker, on the skin of the patient. At every subsequent session, that portion of the body is re-positioned to the position and orientation determined at the first session, by directing the same four laser beams toward the same portion of the body and repositioning that portion, until the four permanent marks line up with the four laser beams.

SUMMARY OF THE DISCLOSED TECHNIQUE

It is an object of the disclosed technique to provide a novel method and system for registering an image acquired in one coordinate system, with another image acquired in another coordinate system.

In accordance with the disclosed technique, there is thus provided a system for registering a first image with a second image. The system includes a first medical positioning system for detecting a first position and orientation of the body of a patient, a second medical positioning system for detecting a second position and orientation of the body, and a registering module. The registering module is coupled with a second imager and with the second medical positioning system.

The first medical positioning system is associated with and coupled with a first imager. The first imager acquires the first image from the body and produces the first image by associating the first image with the first position and orientation. The second medical positioning system is associated with and coupled with the second imager. The second imager acquires the second image and associates the second image with the second position and orientation. The registering module registers the first image with the second image, according to the first position and orientation and the second position and orientation.

Additionally, the system can include an image database coupled with the first imager and with the registering module. The first imager stores the data respective of the first image acquired in the first coordinate system in the image database and the registering module retrieves this data from the image database, in order to register the first image with the second image.

In accordance with another aspect of the disclosed technique, there is thus provided a method for registering a first image with a second image. The method includes the procedures of detecting a first position and orientation of the body of a patient, in a first coordinate system, by a first medical positioning system and determining a first set of coordinates of the first image in the first coordinate system.

The method further includes the procedures of detecting a second position and orientation of the body, in a second coordinate system, by a second medical positioning system and determining a second set of coordinates of the second image in the second coordinate system. The method further includes the procedure of registering the first set of coordinates with the second set of coordinates.

In accordance with a further aspect of the disclosed technique, there is thus provided a system for re-positioning a portion of the body of a patient at the same therapeutic position and orientation suitable for a therapeutic device to medically treat a selected tissue of the body automatically, during multiple therapeutic sessions. The system includes a positioning user interface, a position and orientation detector and a medical positioning system.

The position and orientation detector is located at a selected location associated with the selected tissue. The medical positioning system is coupled with a storage unit, the positioning user interface and with the position and orientation detector. The medical positioning system detects an initial position and orientation of the position and orientation detector, while the selected tissue is placed in the therapeutic position and orientation. The medical positioning system indicates via the positioning user interface when the position and orientation detector is placed again in the initial position and orientation, thereby establishing that the selected tissue is placed again in the therapeutic position and orientation.

In accordance with another aspect of the disclosed technique, there is thus provided a method for re-positioning a portion of the body of a patient during a multi-session automatic therapeutic procedure. The method includes the procedures of detecting an initial position and orientation of a position and orientation detector, and recording the initial position and orientation. The method further includes the procedures of detecting the current position and orientation of the position and orientation detector, at the beginning of each recurring medical treatment and indicating whether the current position and orientation is substantially the same as the recorded position and orientation. The initial position and orientation is associated with a therapeutic position and orientation, suitable for automatically treating a selected tissue of the body.

In accordance with a further aspect of the disclosed technique, there is thus provided a system for medically treating a selected tissue within the body of a patient. The system includes a first medical positioning system, a second medical positioning system and a registering module coupled with the second medical positioning system and with a therapeutic device.

The first medical positioning system detects a first position and orientation of a position and orientation detector in a first coordinate system, when the position and orientation detector is coupled with the first medical positioning system. The position and orientation detector is located at a selected location associated with the selected tissue. The second medical positioning system detects a second position and orientation of the position and orientation detector in a second coordinate system, when the position and orientation detector is coupled with the second medical positioning system.

The registering module registers a set of coordinates of the selected tissue in the first coordinate system, with the second coordinate system, wherein the set of coordinates is associated with the first position and orientation. The therapeutic device, then medically treats the selected tissue according to the registered set of coordinates.

In accordance with another aspect of the disclosed technique, there is thus provided a method for medically treating a selected tissue within the body of a patient. The method includes the procedures of detecting a first position and orientation of a detector in a first coordinate system, by a first medical positioning system, and associating a set of coordinates of the selected tissue in the first coordinate system, with the first position and orientation.

The method further includes the procedures of detecting a second position and orientation of the detector in a second coordinate system, by a second medical positioning system, and registering the associated set of coordinates with the second coordinate system, according to the second position and orientation. The detector is located at a selected location associated with the selected tissue.

In accordance with a further aspect of the disclosed technique, there is thus provided a system for adjusting an imager by means of a moving mechanism, to a desired orientation with respect to a section of the body of a patient, to acquire a visual representation of the section of the body. The visual representation includes an optimal representation of a portion of interest of a medical intervention device. The medical intervention device is inserted into the section of the body of the patient.

The system includes a medical positioning system, a processor coupled with the medical positioning system and with the moving mechanism, and a device position and orientation detector coupled with the medical intervention device at the portion of interest and with the medical positioning system. The medical positioning system detects a device position and orientation of the device position and orientation detector. The medical positioning system provides the device position and orientation to the processor. The processor determines the desired orientation, according to the detector position and orientation, and the processor directs the moving mechanism to move the imager to the desired orientation.

Additionally, the system can include an imager position and orientation detector coupled with the imager and with the medical positioning system. The medical positioning system detects an imager position and orientation of the imager and provides the imager position and orientation to the processor. The processor determines the desired orientation, according to the device position and orientation and the imager position and orientation.

In accordance with another aspect of the disclosed technique, there is thus provided a method for adjusting an imager to a desired orientation to acquire a visual representation of a section of the body of a patient. The visual representation includes an optimal representation of a portion of interest of a medical intervention device. The method includes the procedures of detecting a device position and orientation of a position and orientation detector coupled with the medical intervention device, at the portion of interest, and determining the desired orientation according to the device position and orientation, such that the imager can acquire the visual representation. The method further includes the procedure of directing a moving mechanism to move the imager to the desired orientation. The method can further include the procedures of detecting an imager position and orientation of an imager position and orientation detector coupled with the imager and determining the position and orientation of the imager from the imager position and orientation.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a non-visual registering system and method. The method of disclosed technique basically includes non-visually determining the coordinates of a first image in a first coordinate system, non-visually determining the coordinates of a second image in a second coordinate system and registering the first image with the second coordinate system, according to the determined coordinates. When the scaling of the first coordinate system and the scaling of the second coordinate system are not the same, the scale of the first image is modified to match that of the second coordinate system, such that when the first image and the second image are presented together, they are on the same scale. Furthermore, a representation of a medical intervention device, such as catheter, needle, forceps, and the like, can be superimposed on the first image, by detecting the position and orientation of the medical intervention device, via a detector attached to the medical intervention device.

In the following description, a coordinate system can be orthogonal, polar, cylindrical, and the like. It is noted that the term "image" herein below, refers to any type of visual representation of a selected portion of the body of the patient, either acquired directly or reconstructed from raw measurements. Such an image can be provided in one, two or three spatial dimensions, still image or developing in time. It is noted that any of the MPS systems mentioned herein below may be coupled with the device or system associated therewith, either physically (i.e., in a fixed location with respect thereto) or logically (i.e., where both collaborate within the same coordinate system). In the following description, a medical intervention device can be a catheter (e.g., balloon catheter, stent catheter, surgical catheter, dilution catheter), drug delivery unit (e.g., needle, catheter having a coated stent or a balloon, brachytherapy unit), tissue severing unit (e.g., forceps, ablation catheter), and the like.

Figure 1A:
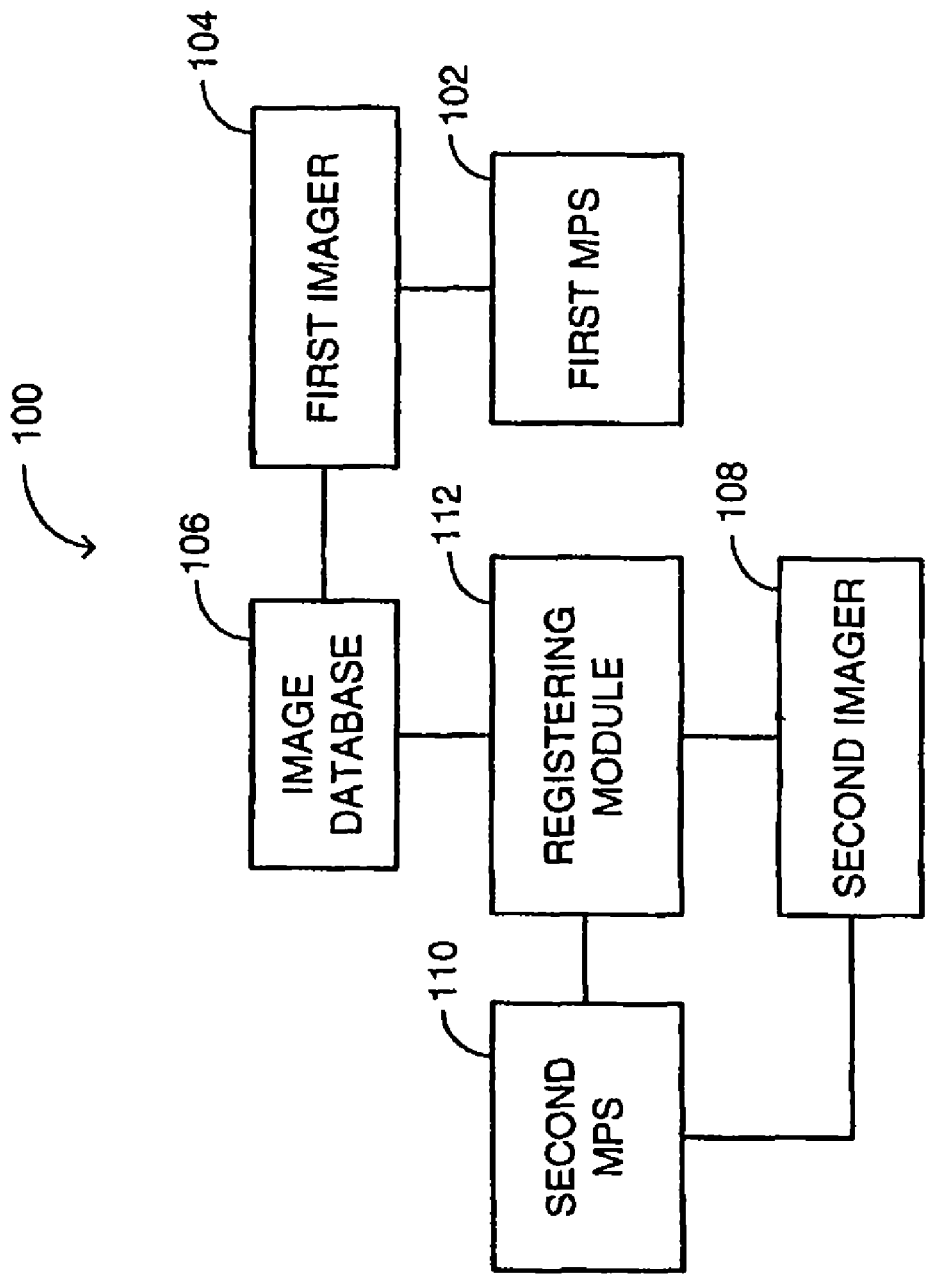
FIG. 1A is a schematic illustration of a system for registering a first image acquired by a first imager, with a second image acquired by a second imager, constructed and operative according to an embodiment of the disclosed technique.
Figure 1B:
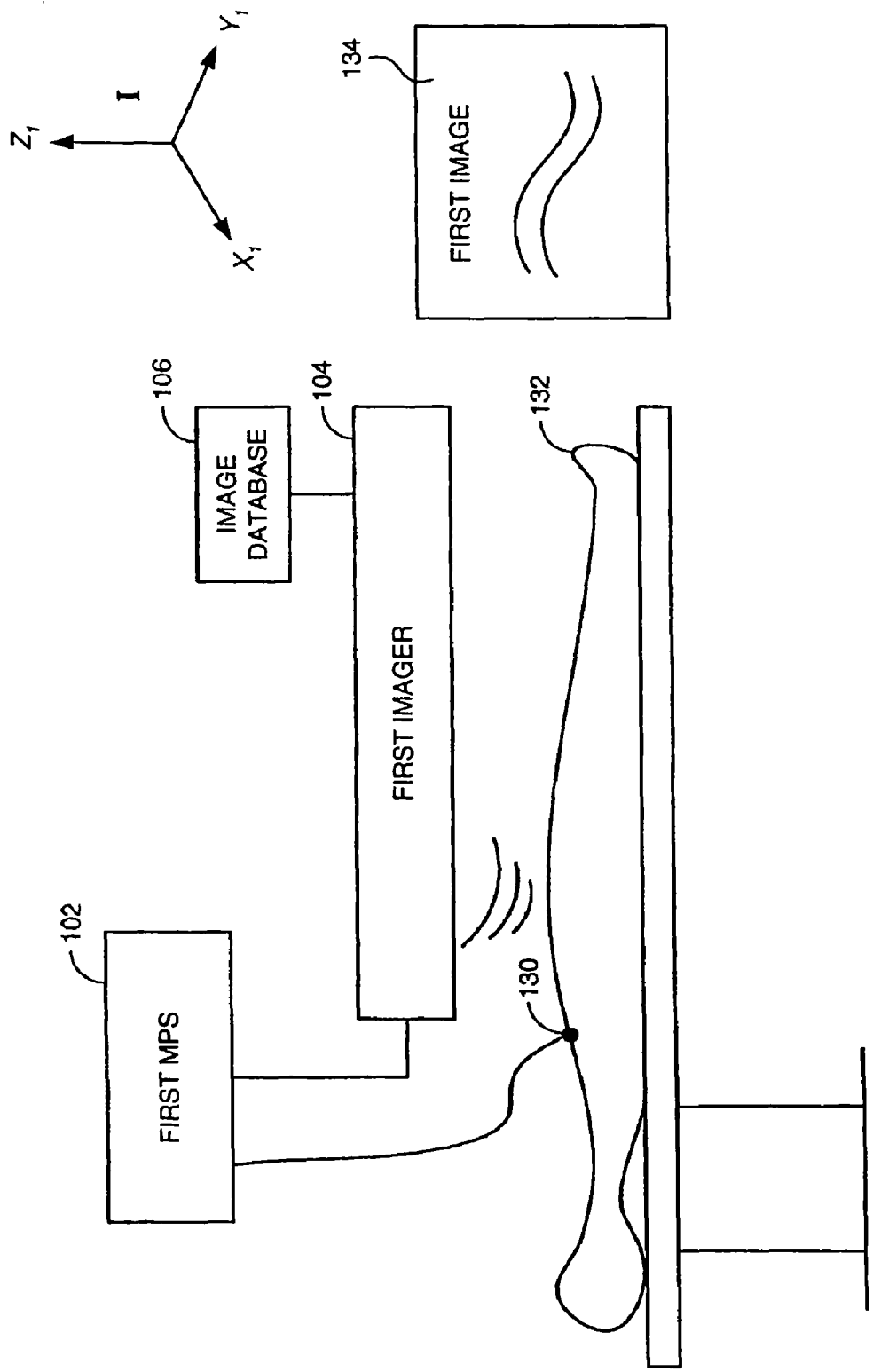
FIG. 1B is a schematic illustration of a portion of the system of FIG. 1A, which acquires the first image.
Figure 1C:
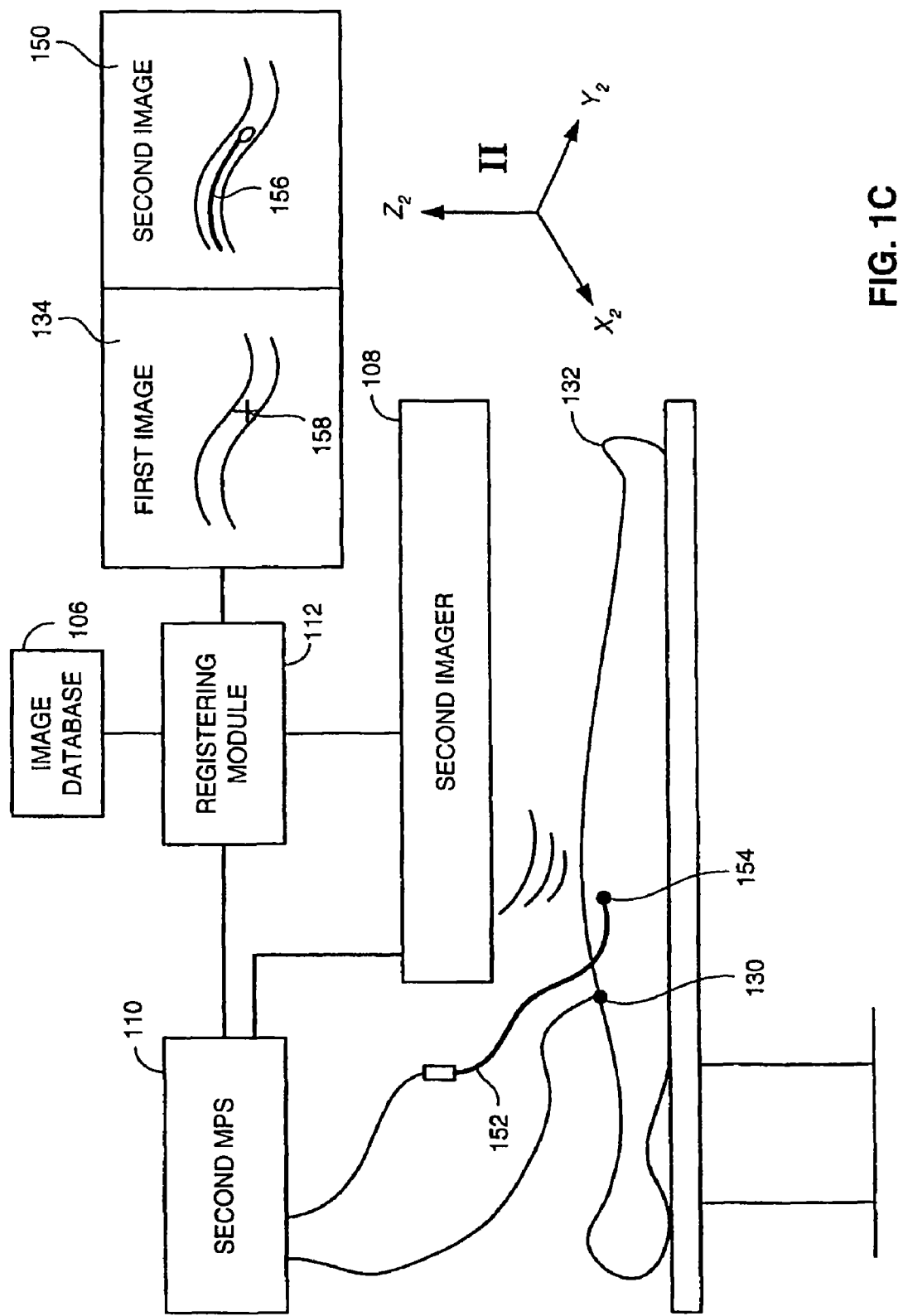
FIG. 1C is a schematic illustration of another portion of the system of FIG. 1A, which acquires the second image and registers the first image with the second image.
Figure 1D:
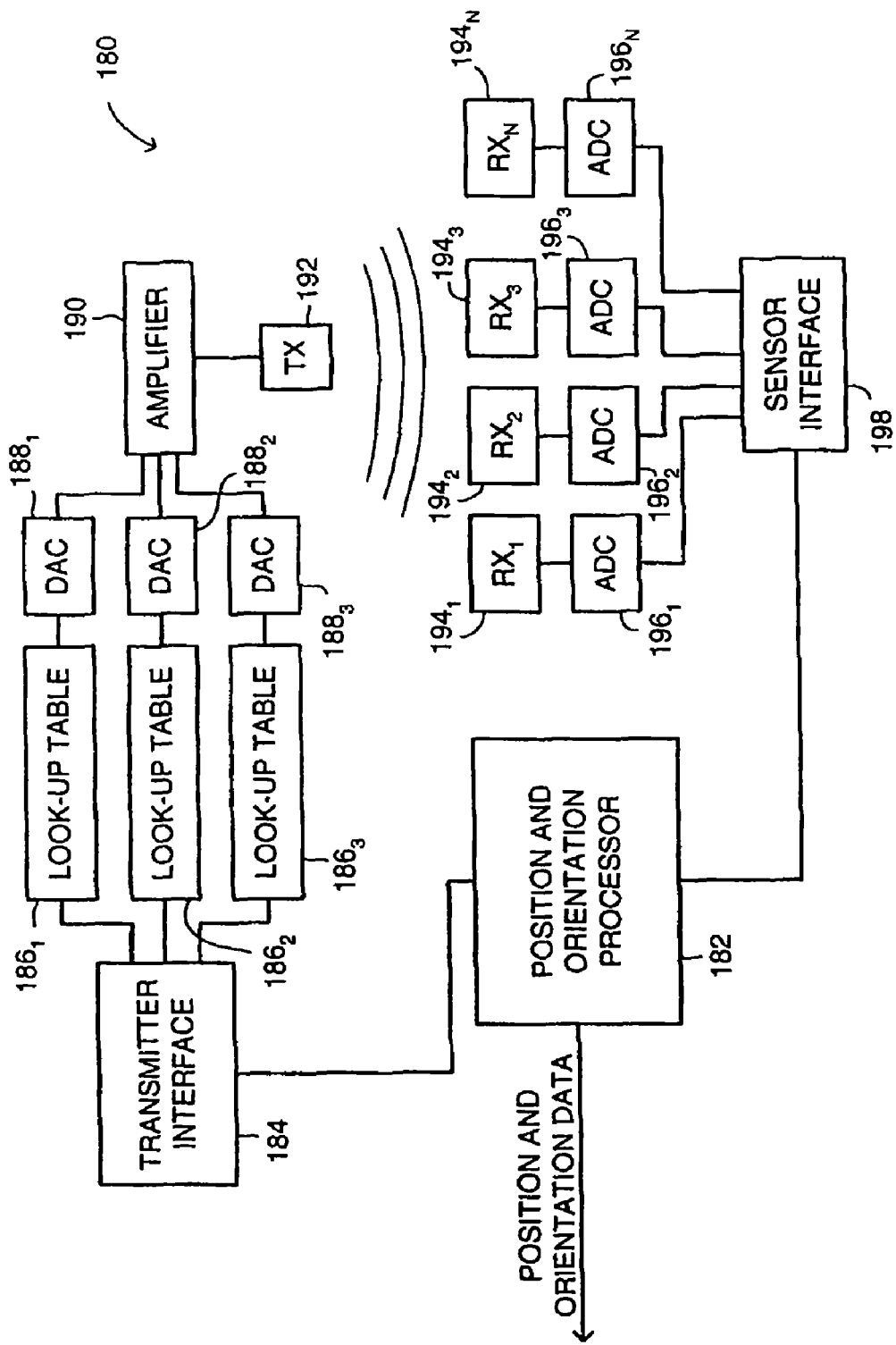
FIG. 1D is a schematic illustration of each of the first medical positioning system (MPS) and the second MPS of the system of FIG. 1A.

Reference is now made to FIGS. 1A, 1B, 1C and 1D. FIG. 1A, is a schematic illustration of a system for registering a first image acquired by a first imager, with a second image acquired by a second imager, generally referenced 100, constructed and operative according to an embodiment of the disclosed technique. FIG. 1B, is a schematic illustration of a portion of the system of FIG. 1A, which acquires the first image. FIG. 1C, is a schematic illustration of another portion of the system of FIG. 1A, which acquires the second image and registers the first image with the second image. FIG. 1D, is a schematic illustration of each of the first medical positioning system (MPS) and the second MPS of the system of FIG. 1A, generally referenced 180.

With reference to FIG. 1A, system 100 includes a first MPS 102, a first imager 104, an image database 106, a second imager 108, a second MPS 110 and a registering module 112. Each of first MPS 102 and second MPS 110 is a device which determines the position and orientation of a three-dimensional body (not shown), according to a signal received from a position and orientation detector (not shown), which is attached to the three-dimensional body. Each of first MPS 102 and second MPS 110 is similar to the MPS of U.S. Pat. No. 6,233,476, which is herein incorporated by reference. Each of first MPS 102 and second MPS 110 can be replaced by a position and orientation determining device which determines the position and orientation of the three-dimensional body by performing a triangulation operation on signals received from a plurality of detectors. These alternative position and orientation determining devices are described herein below in connection with FIGS. 4 and 5.

Image database 106 is a data storage unit, such as magnetic memory unit (e.g., floppy diskette, hard disk, magnetic tape), optical memory unit (e.g., compact disk), volatile electronic memory unit (e.g., random access memory), non-volatile electronic memory unit (e.g., read only memory, flash memory), remote network storage unit, and the like. Each of first imager 104 and second imager 108 is a device which acquires an image of the body of a patient (not shown), (e.g., fluoroscopy, ultrasound, nuclear magnetic resonance—NMR, optical imaging, thermography, nuclear imaging—PET). Registering module 112 is a module which registers the first image with the second image.

First imager 104 is coupled with first MPS 102 and with image database 106. Second imager 108 is coupled with second MPS 110. Registering module 112 is coupled with image database 106, second imager 108 and with second MPS 110.

Alternatively, the system includes a plurality of medical systems (e.g., imager, automated therapeutic system), each associated with an MPS system and all coupled together via a network (e.g., LAN, WAN, wired or wireless). It is noted that each of these MPS systems is spatially calibrated with the respective medical system associate therewith, such that both either share the same coordinate system or are able to translate between the medical system coordinate system and the MPS system coordinate system.

With reference to FIG. 1B, a body position and orientation detector 130 is attached to the body of a patient 132. Body position and orientation detector 130 is similar to the sensor of U.S. Pat. No. 6,233,476 which is herein incorporated by reference. Body position and orientation detector 130 is either attached to the skin (not shown) of patient 132, placed under the skin, or implanted within the body of patient 132. Thus, body position and orientation detector 130 is fixed to the body of patient 132. First MPS 102 is coupled with body position and orientation detector 130 and with first imager 104. First imager 104 is coupled with image database 106.

First MPS 102 is associated with an $X_1, Y_1, Z_1$ coordinate system (i.e., coordinate system I). First imager 104 is calibrated with first MPS 102, such that the position and orientation of first imager 104 is defined relative to coordinate system I. Body position and orientation detector 130 provides a signal respective of the position and orientation thereof, to first MPS 102. First MPS 102 determines the position and orientation of body position and orientation detector 130 in coordinate system I, according to the signal received from body position and orientation detector 130. First MPS 102 provides a signal respective of the position and orientation of body position and orientation detector 130, to first imager 104. First imager 104 acquires a first image 134 of the body of patient 132 and stores in image database 106, the set of coordinates of first image 134 in coordinate system I, together with the coordinates of body position and orientation detector 130 in coordinate system I.

Generally, this portion of system 100 (i.e., the stage of acquisition of first image 134 from the body of patient 132), is performed prior to performing a medical operation on patient 132. Hence, the image acquisition stage as illustrated in FIG. 1B can be performed at a physical location different than that of the image acquisition and medical operation stage, as illustrated in FIG. 1C.

With reference to FIG. 1C, second MPS 110 is coupled with body position and orientation detector 130, device position and orientation detector 154, second imager 108 and with registering module 112. Registering module 112 is coupled with image database 106 and with second imager 108.

Second imager 108 acquires a second image (e.g., a second image 150) of the body of patient 132, while a clinical staff performs the medical operation on patient 132. Second MPS 110 is associated with an $X_2$, $Y_2$, $Z_2$ coordinate system (i.e., coordinate system II). Second imager 108 is calibrated with second MPS 110, such that the position and orientation of second imager 108 is defined relative to coordinate system II.

Body position and orientation detector 130 provides a signal respective of the position and orientation thereof, to second MPS 110. Second MPS 110 determines the position and orientation of the body position and orientation detector 130 in coordinate system II, according to the signal received from body position and orientation detector 130. Second MPS 110 provides a signal respective of the position and orientation of body position and orientation detector 130, to second imager 108. Second imager 108 associates the set of coordinates of second image 150 in coordinate system II, with the position and orientation of position and orientation detector 130 in coordinate system II and provides a respective signal to registering module 112.

Registering module 112 retrieves from image database 106, the data respective of the set of coordinates of first image 134 in coordinate system I, and the coordinates of body position and orientation detector 130 in coordinate system I. Registering module 112 registers the position and orientation of body position and orientation detector 130 in coordinate system I, with the position and orientation of body position and orientation detector 130 in coordinate system II. In this manner, registering module 112 registers first image 134, which was originally acquired in coordinate system I, with coordinate system II, such that both first image 134 and second image 150 can be presented together within the same coordinate system II. It is noted that registering module 112 registers first image 134 with second image 150, by employing a position and orientation detector and without any visible marks or visible markers.

In case the scale of coordinate system I is not exactly the same as that of coordinate system II, registering module 112 can change the scale of first image 134 according to the scale factor between coordinate system I and coordinate system II. This scale factor is stored in registering module 112. For this purpose, more than one position and orientation detector similar to body position and orientation detector 130, can be employed, as described herein below, in connection with FIG. 3A.

Body position and orientation detector 130 is secured to a selected point on or within the body of patient 132 and maintains substantially the same position and orientation relative to body of patient 132. Body position and orientation detector 130 can be wired and include a connector (not shown), in order to disconnect body position and orientation detector 130 from first MPS 102 and connect body position and orientation detector 130 to second MPS 110. Alternatively, the body position and orientation detector can be wireless.

Prior to, or during image acquisition by second imager 108, a medical intervention device 152 may be inserted into the body of patient 132. A device position and orientation detector 154 is coupled with medical intervention device 152. In the example set forth in FIG. 1C, medical intervention device 152 is a catheter, and device position and orientation detector 154 is located at a distal end of the catheter. In the example set forth in FIG. 1A, first imager 104 is a CT device and second imager 108 is an X-ray device.

Device position and orientation detector 154 provides a signal respective of the position and orientation of the distal end of the catheter, to second MPS 110. Second MPS 110 determines the position and orientation of the distal end of the catheter in coordinate system II, according to the signal received from device position and orientation detector 154. Second MPS 110 provides a signal respective of the position and orientation of the distal end of the catheter, to registering module 112.

Since in the example of FIG. 1C, second imager 108 is an X-ray device and the catheter is made of a radiopaque material, second image 150 includes a real time image 156 of the catheter as well as an image of the body of patient 132.

Registering module 112 can be adapted either to merely transform and scale coordinates from a coordinate system I to coordinate system II or to provide image processing (e.g., superimposing images, adding visual representations of devices). For example, registering module 112 can superimpose a real time representation 158 of the distal end of medical intervention device 152 on first image 134, according to the signal received from second MPS 110. Registering module 112 provides a video signal respective of first image 134 and second image 150 to a display (not shown) and the display displays first image 134 alongside second image 150. Thus, the clinical staff can view real time image 156 of medical intervention device 152 in second image 150 alongside real time representation 158 of medical intervention device 152 in first image 134.

In another example, registering module 112 superimposes first image 134 on second image 150, after registering first image 134 with in coordinate system II. In this case, the superimposed image (not shown) includes the first image, the second image, and either the real time image of medical intervention device or the real time visual representation of medical intervention device.

With reference to FIG. 1D MPS 180 includes a position and orientation processor 182, a transmitter interface 184, a plurality of look-up table units $186_1$, $186_2$ and $186_3$, a plurality of digital to analog converters (DAC) $188_1$, $188_2$ and $188_3$, an amplifier 190, a transmitter 192, a plurality of MPS sensors $194_1$, $194_2$, $194_3$ and $194_N$ (i.e., position and orientation detectors), a plurality of analog to digital converters (ADC) $196_1$, $196_2$, $196_3$ and $196_N$ and a sensor interface 198.

Transmitter interface 184 is coupled with position and orientation processor 182 and with look-up table units $186_1$, $186_2$ and $186_3$. DAC units $188_1$, $188_2$ and $188_3$ are coupled with a respective one of look-up table units $186_1$, $186_2$ and $186_3$ and with amplifier 190. Amplifier 190 is further coupled with transmitter 192. Transmitter 192 is also marked TX. MPS sensors $194_1$, $194_2$, $194_3$ and $194_N$ are further marked $RX_1$, $RX_2$, $RX_3$ and $RX_N$, respectively.

Analog to digital converters (ADC) $196_1$, $196_2$, $196_3$ and $196_N$ are respectively coupled with sensors $194_1$, $194_2$, $194_3$ and $194_N$ and with sensor interface 198. Sensor interface 198 is further coupled with position and orientation processor 182.

Each of look-up table units $186_1$, $186_2$ and $186_3$ produces a cyclic sequence of numbers and provides it to the respective DAC unit $188_1$, $188_2$ and $188_3$, which in turn translates it to a respective analog signal. Each of the analog signals is respective of a different spatial axis. In the present example, look-up table $186_1$ and DAC unit $188_1$ produce a signal for the X axis, look-up table $186_2$ and DAC unit $188_2$ produce a signal for the Y axis and look-up table $186_3$ and DAC unit $188_3$ produce a signal for the Z axis.

DAC units $188_1$, $188_2$ and $188_3$ provide their respective analog signals to amplifier 190, which amplifies and provides the amplified signals to transmitter 192. Transmitter 192 provides a multiple axis electromagnetic field, which can be detected by MPS sensors $194_1$, $194_2$, $194_3$ and $194_N$. Each of MPS sensors $194_1$, $194_2$, $194_3$ and $194_N$ detects an electromagnetic field, produces a respective electrical analog signal and provides it to the respective ADC unit $196_1$, $196_2$, $196_3$ and $196_N$ coupled therewith. Each of the ADC units $196_1$, $196_2$, $196_3$ and $196_N$ digitizes the analog signal fed thereto, converts it to a sequence of numbers and provides it to sensor interface 198, which in turn provides it to position and orientation processor 182.

Position and orientation processor 182 analyzes the received sequences of numbers, thereby determining the position and orientation of each of the MPS sensors $194_1$, $194_2$, $194_3$ and $194_N$. Position and orientation processor 182 further determines distortion events and updates look-up tables $186_1$, $186_2$ and $186_3$, accordingly.

According to another aspect of the disclosed technique, a processor associates each of a plurality of two-dimensional images acquired by a first imager, with the position and orientation of the body of the patient and with the position of each two-dimensional image in an organ timing signal (e.g., ECG) acquired by a first organ timing monitor. The processor reconstructs a plurality of three-dimensional images from the two-dimensional images, according to the respective position and orientation of each two-dimensional image and its position within the organ timing signal and the processor stores the reconstructed three-dimensional images in an image database. A registering module retrieves a three-dimensional image from the image database according to the current time point detected by a second organ timing monitor and the registering module registers the retrieved three-dimensional image with another image acquired by a second imager.

Figure 2A:
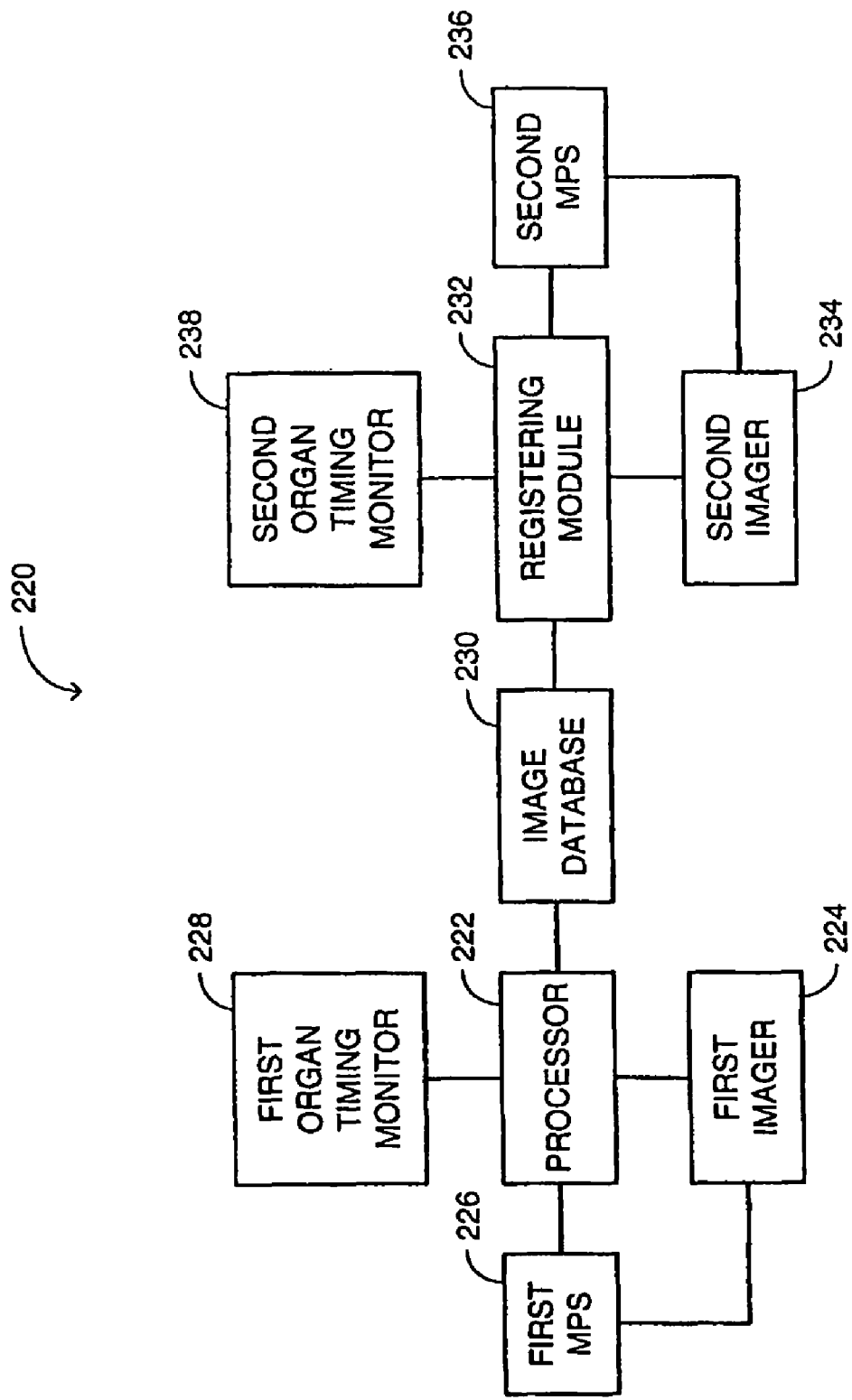
FIG. 2A is a schematic illustration of a system for registering a first reconstructed image with a second image acquired by a second imager, constructed and operative according to another embodiment of the disclosed technique.
Figure 2B:
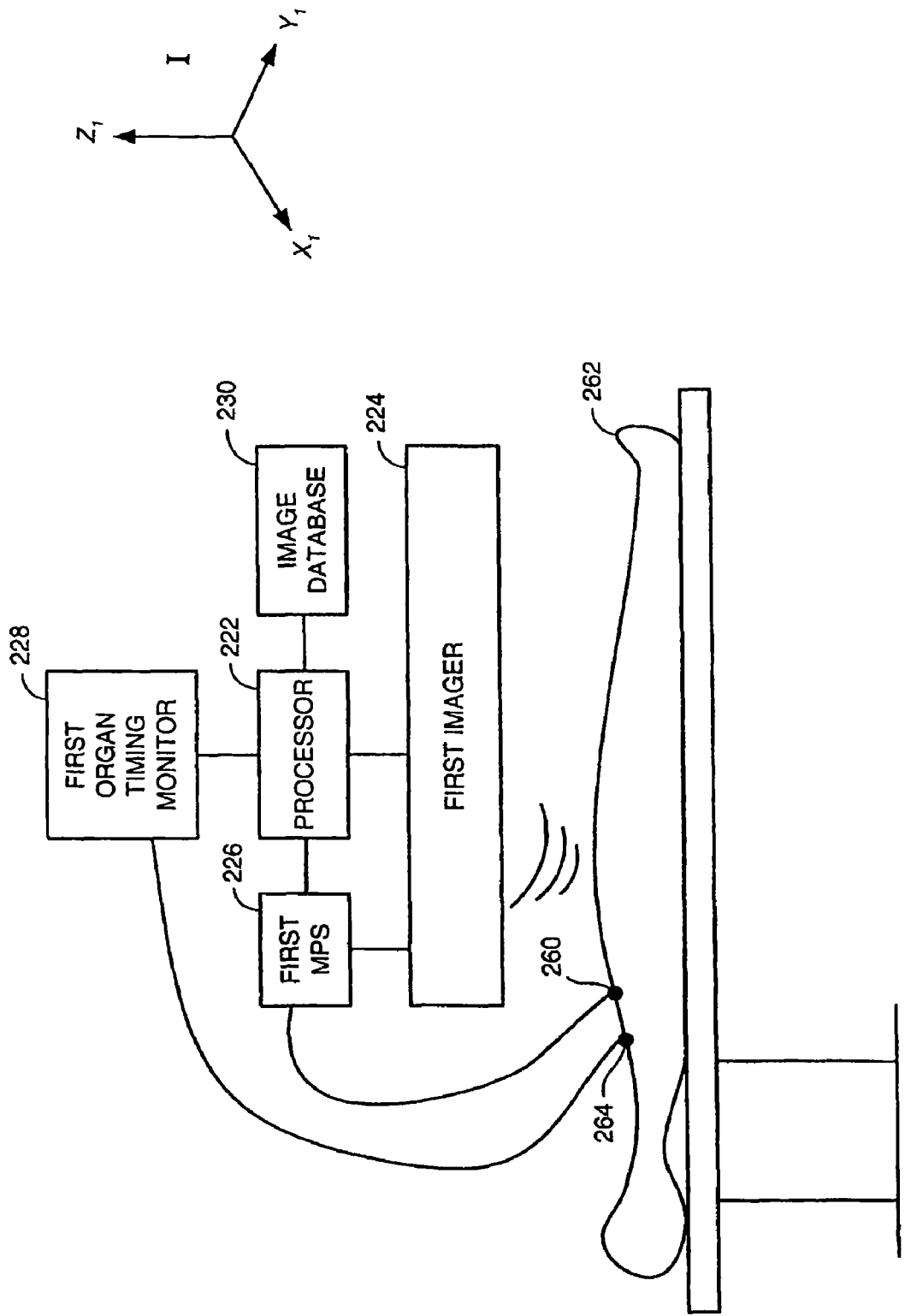
FIG. 2B is a schematic illustration of a portion of the system of FIG. 2A, which reconstructs the first reconstructed image from a plurality of two-dimensional images.
Figure 2C:
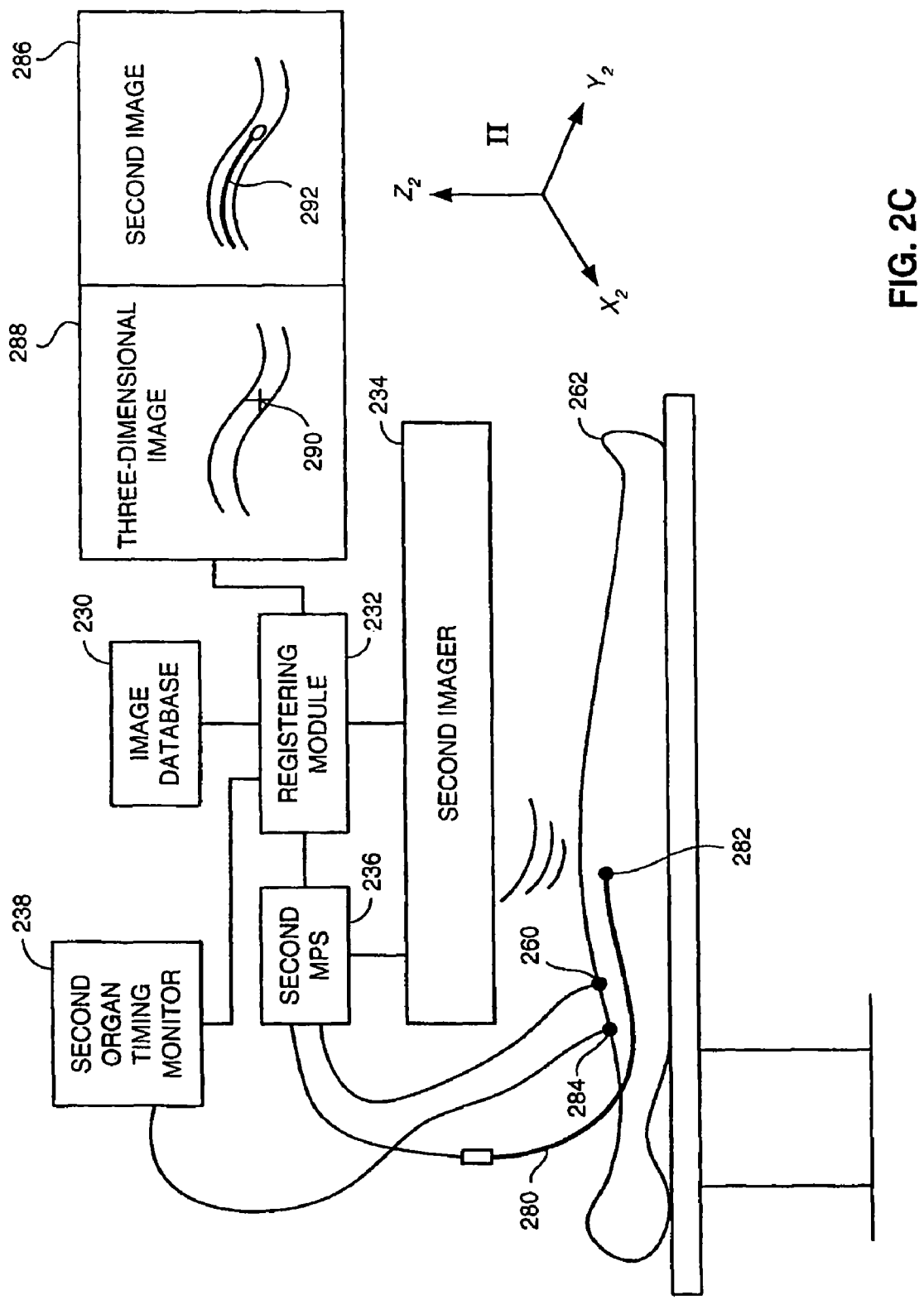
FIG. 2C is a schematic illustration of another portion of the system of FIG. 2A, which acquires the second image and registers the first reconstructed image with the second image.
Figure 2D:
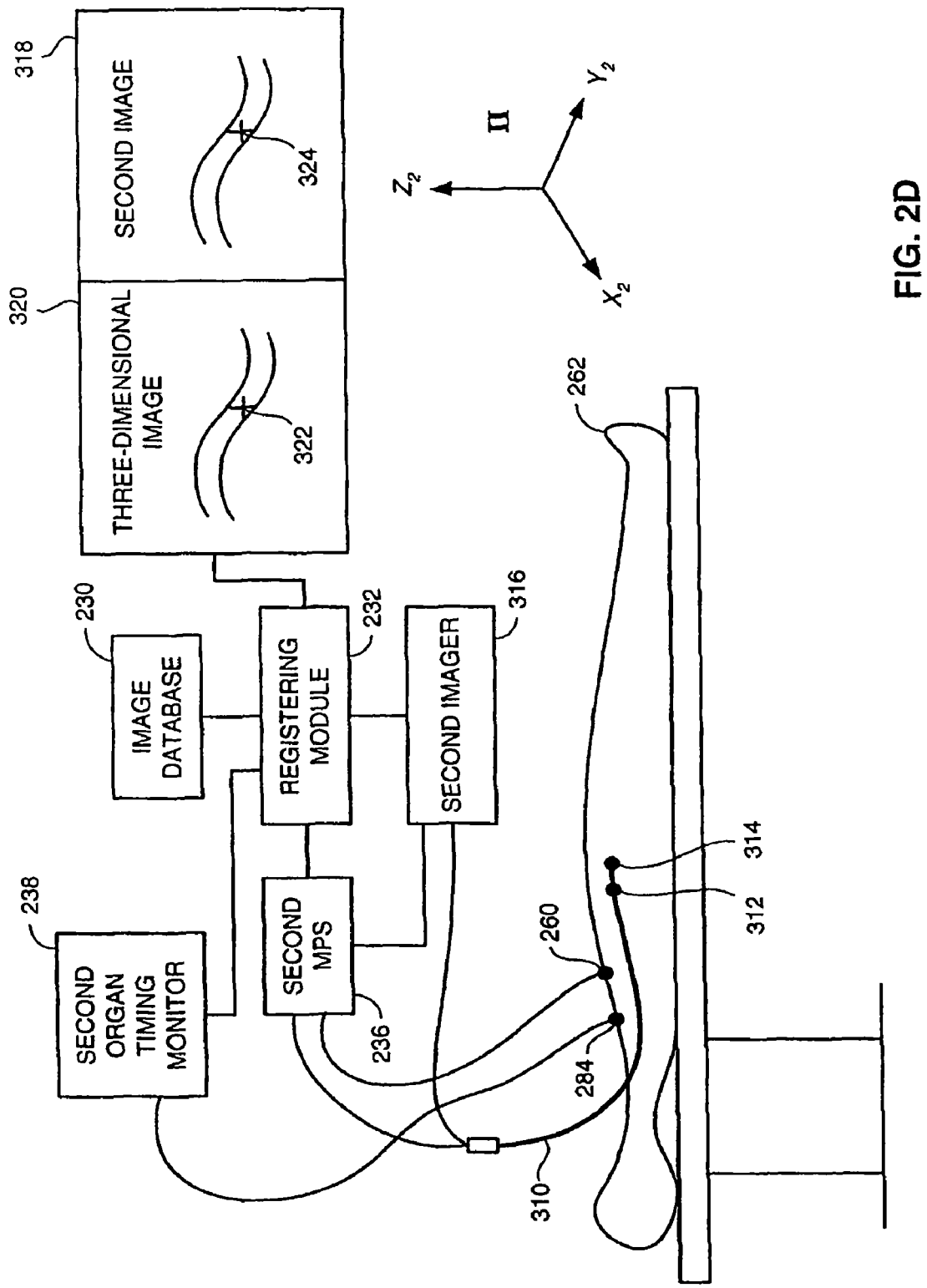
FIG. 2D is a schematic illustration of the portion of the system of FIG. 2A, which acquires the second image by an image detector which is attached to a medical intervention device, and wherein this portion of the system registers the first reconstructed image with the second image.

Reference is now made to FIGS. 2A, 2B, 2C and 2D. FIG. 2A, is a schematic illustration of a system for registering a first reconstructed image with a second image acquired by a second imager, generally referenced 220, constructed and operative according to another embodiment of the disclosed technique. FIG. 2B, is a schematic illustration of a portion of the system of FIG. 2A, which reconstructs the first reconstructed image from a plurality of two-dimensional images. FIG. 2C, is a schematic illustration of another portion of the system of FIG. 2A, which acquires the second image and registers the first reconstructed image with the second image. FIG. 2D, is a schematic illustration of the portion of the system of FIG. 2A, which acquires the second image by an image detector which is attached to a medical intervention device, and wherein this portion of the system registers the first reconstructed image with the second image.

With reference to FIG. 2A, system 220 includes a processor 222, a first imager 224, a first MPS 226, a first organ timing monitor 228, an image database 230, a registering module 232, a second imager 234, a second MPS 236 and a second organ timing monitor 238. Processor 222 is similar to the main computer of U.S. patent application Ser. No. 09/782,528, which is herein incorporated by reference. First imager 224 and second imager 234 are similar to first imager 104 and second imager 108, as described herein above in connection with FIG. 1A. Each of first organ timing monitor 228 and second organ timing monitor 238 is a device for monitoring the pulse rate of an inspected organ, such as the heart, the lungs, the eyelids, and the like. Each of first MPS 226 and second MPS 236 is similar to MPS 180, as described herein above in connection with FIG. 1D.

Processor 222 is coupled with first imager 224, first MPS 226 first organ timing monitor 228 and with image database 230. First imager 224 is coupled with first MPS 226. Registering module 232 is coupled with second imager 234, second MPS 236, second organ timing monitor 238 and with image database 230. Second imager 234 is coupled with second MPS 236.

With reference to FIG. 2B, an organ timing sensor 260 is attached to the body of a patient 262, similar in the way that body position and orientation detector 130 (FIG. 1B) is attached to the body of patient 132. A first pulse sensor 264 is attached to an organ (not shown) of patient 262, such as the heart, lungs, eyelids and the like. Organ timing sensor 260 is coupled with first MPS 226. First pulse sensor 264 is coupled with first organ timing monitor 228. Processor 222 is coupled with first imager 224, first MPS 226, first organ timing monitor 228 and with image database 230. First imager 224 is coupled with first MPS 226.

First MPS 226 determines the position and orientation of organ timing sensor 260 in an $X_1$, $Y_1$, $Z_1$ coordinate system (i.e., coordinate system I), according to a signal received from organ timing sensor 260. First MPS 226 provides a signal respective of the determined position and orientation of organ timing sensor 260, to processor 222 and to first imager 224. First imager 224 acquires a plurality of two-dimensional images from the body of patient 262 and associates each of the acquired two-dimensional images with the determined position and orientation of organ timing sensor 260. First imager 224 provides a signal respective of the associated two-dimensional images to processor 222. First organ timing monitor 228 determines the timing signal of the organ of patient 262, according to a signal received from first pulse sensor 264 and first organ timing monitor 228 provides a signal respective of the timing signal to processor 222. The timing signal can be for example, the QRS wave of the heart (not shown).

Processor 222 associates each of the two-dimensional images with the current time point of the timing signal. Processor 222 reconstructs a plurality of three-dimensional images from the two-dimensional images, according to the position and orientation of organ timing sensor 260 and according to the time points of the timing signal. Processor 222 stores the reconstructed three-dimensional images in image database 230.

With reference to FIG. 2C, registering module 232 is coupled with second imager 234, second MPS 236, second organ timing monitor 238 and with image database 230. Second imager 234 is coupled with second MPS 236. Organ timing sensor 260 and device position and orientation detector 282 are coupled with second MPS 236. Second pulse sensor 284 is coupled with second organ timing monitor 238.

A medical intervention device 280 is inserted into the body of patient 262. In the example set forth in FIG. 2C, medical intervention device 280 is a catheter. A device position and orientation detector 282 is located at a distal end of medical intervention device 280. Device position and orientation detector 282 detects the position and orientation of the distal end of medical intervention device 280. A second pulse sensor 284 is attached to the same organ of patient 262, to which first pulse sensor 264 was attached. It is noted that first pulse sensor 264 and first organ timing monitor 228 can be employed in the embodiment of FIG. 2C, instead of second pulse sensor 284 and second organ timing monitor 238, respectively.

Second MPS 236 determines the position and orientation of organ timing sensor 260 in an $X_2, Y_2, Z_2$ coordinate system (i.e., coordinate system II), according to a signal received from organ timing sensor 260. Second MPS 236 further determines the position and orientation of the distal end of medical intervention device 280, according to a signal received from device position and orientation detector 282. Second MPS 236 provides a signal respective of the determined position and orientation of organ timing sensor 260, to registering module 232 and to second imager 234. Second MPS 236 provides a signal respective of the determined position and orientation of the distal end of medical intervention device 280, to registering module 232.

Second imager 234 acquires a second image (e.g., a second image 286 as illustrated in FIG. 2C), from the body of patient 262 and associates the second image with the determined position and orientation of the body of patient 262. Second imager 234 provides a signal respective of the associated second image to registering module 232. Second organ timing monitor 238 determines the timing signal of the organ of patient 262, according to a signal received from second pulse sensor 284 and second organ timing monitor 238 provides a signal respective of the timing signal to registering module 232.

Registering module 232 retrieves a three-dimensional image (e.g., a three-dimensional image 288 as illustrated in FIG. 2C) from image database 230, according to the determined position and orientation of the body of patient 262 and according to the current time point of the determined timing signal. Registering module 232 registers three-dimensional image 288, which was acquired in coordinate system I, with coordinate system II which already includes second image 286, which was acquired in coordinate system II, in a similar manner as described herein above in connection with first image 134 (FIG. 1C) and second image 150.

Registering module 232 produces different combinations of three-dimensional image 288, second image 286, a visual representation of the distal end of medical intervention device 280 and a real time image of medical intervention device 280. For example, registering module 232 superimposes a real time visual representation 290 of the distal end of medical intervention device 280 (in this case a catheter) on the retrieved three-dimensional image, thereby producing three-dimensional image 288. Registering module 232 provides a respective video signal to a display (not shown). The display displays three-dimensional image 288 alongside second image 286.

In another example, registering module 232 superimposes three-dimensional image 288 on second image 286. Second image 286 can include a real time image 292 of medical intervention device 280. In this case, the clinical staff can view a real time visual representation 290 of medical intervention device 280, on a pseudo-real-time three-dimensional image of the organ of the patient 262 (i.e., three-dimensional image 288), wherein three-dimensional image 288 is constantly updated according to the timing signal of the organ. Moreover, the clinical staff can view real time image 292 of medical intervention device 280 on a real time image of the organ (i.e., second image 286) which generally includes less information than the pseudo-real-time three-dimensional image (i.e., three-dimensional image 288).

With reference to FIG. 2D, registering module 232 is coupled with second imager 316, second MPS 236, second organ timing monitor 238 and with image database 230. Second imager 316 is coupled with second MPS 236 and with image detector 314. Device position and orientation detector 312 and organ timing sensor 260 are coupled with second MPS 236. Second pulse sensor 284 is coupled with second organ timing monitor 238.

A medical intervention device 310, such as a catheter, is inserted into the body of patient 262. A body position and orientation detector 312 and an image detector 314 are located at a distal end of medical intervention device 310. Image detector 314 is similar to the image detector of U.S. patent application Ser. No. 09/949,160, which is herein incorporated by reference. Hence, image detector 314 can be an optical coherence tomography (OCT) imaging element, intravascular ultrasound (IVUS) transducer, magnetic resonance imaging (MRI) element, thermography imaging element, angiography imaging element, and the like. A second imager 316 produces a second image (e.g., a second image 318 as illustrated in FIG. 2D), according to a signal received from image detector 314.

Second MPS 236 determines the position and orientation of organ timing sensor 260 in coordinate system II, according to a signal received from organ timing sensor 260. Second MPS 236 determines the position and orientation of the distal end of medical intervention device 310, according to a signal received from device position and orientation detector 312. Second MPS 236 provides a signal respective of the determined position and orientation of organ timing sensor 260, to registering module 232 and to second imager 316. Second MPS 236 provides a signal respective of the determined position and orientation of the distal end of medical intervention device 310, to registering module 232.

Image detector 314 provides a signal to second imager 316, respective of surrounding objects (e.g., the intima of a blood vessel) and second imager 316 produces a second image, such as second image 318, according to the received signal. Second imager 316 associates the second image with the determined position and orientation of organ timing sensor 260. Second imager 316 provides a signal respective of the associated second image to registering module 232. Second organ timing monitor 238 determines the timing signal of the organ of patient 262, according to a signal received from second pulse sensor 284 and second organ timing monitor 238 provides a signal respective of the timing signal to registering module 232.

Registering module 232 retrieves a three-dimensional image (e.g., a three-dimensional image 320 as illustrated in FIG. 2D) from image database 230, according to the determined position and orientation of organ timing sensor 260 and according to the current time point of the determined timing signal. Registering module 232 registers three-dimensional image 320, which was acquired in coordinate system I, with second image 318, which was acquired in coordinate system II, in a similar manner as described herein above in connection with first image 134 (FIG. 1C) and second image 150.

Registering module 232 produces different combinations of three-dimensional image 320, second image 318, a visual representation of the distal end of medical intervention device 310 and a real time image of medical intervention device 310. For example, registering module 232 superimposes a real time visual representation 322 of the distal end of medical intervention device 310 (in this case a catheter) on the retrieved three-dimensional image, thereby producing three-dimensional image 320. Registering module 232 provides a respective video signal to a display (not shown). This display displays three-dimensional image 320 alongside second image 318.

In another example, registering module 232 superimposes three-dimensional image 320 on second image 318. Second image 318 can include a real time visual representation 324 of medical intervention device 310.

Figure 3C:
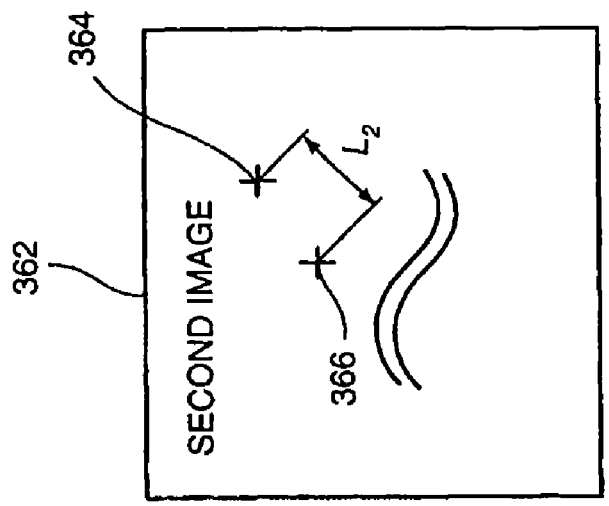
FIG. 3C is a schematic illustration of a second image of the body of the patient, acquired by a second imager similar to the second imager of FIG. 1A, wherein the scale of the second image is different from the scale of the first image of FIG. 3B.
Figure 3B:
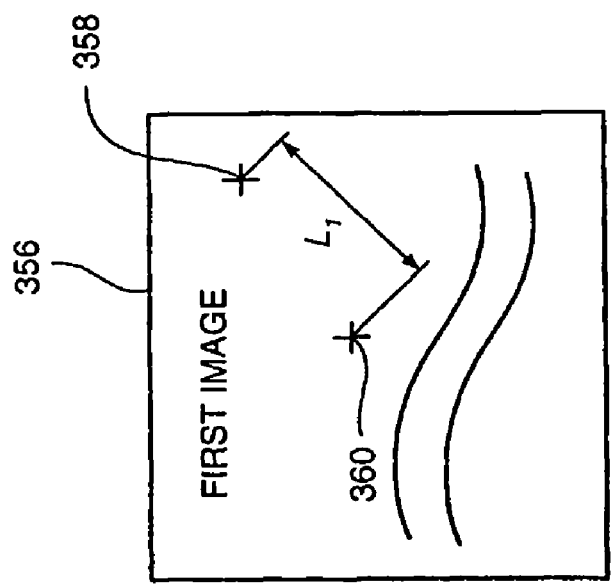
FIG. 3B is a schematic illustration of a first image of the body of the patient, acquired by a first imager, similar to the first imager of FIG. 1A.
Figure 3A:
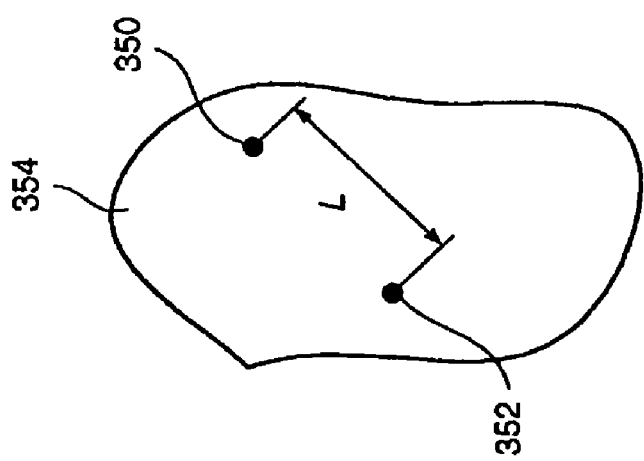
FIG. 3A is a schematic illustration of two body position and orientation detectors arranged on the body of a patient, to determine the scale factor of an image, according to a further embodiment of the disclosed technique.
Figure 3D:
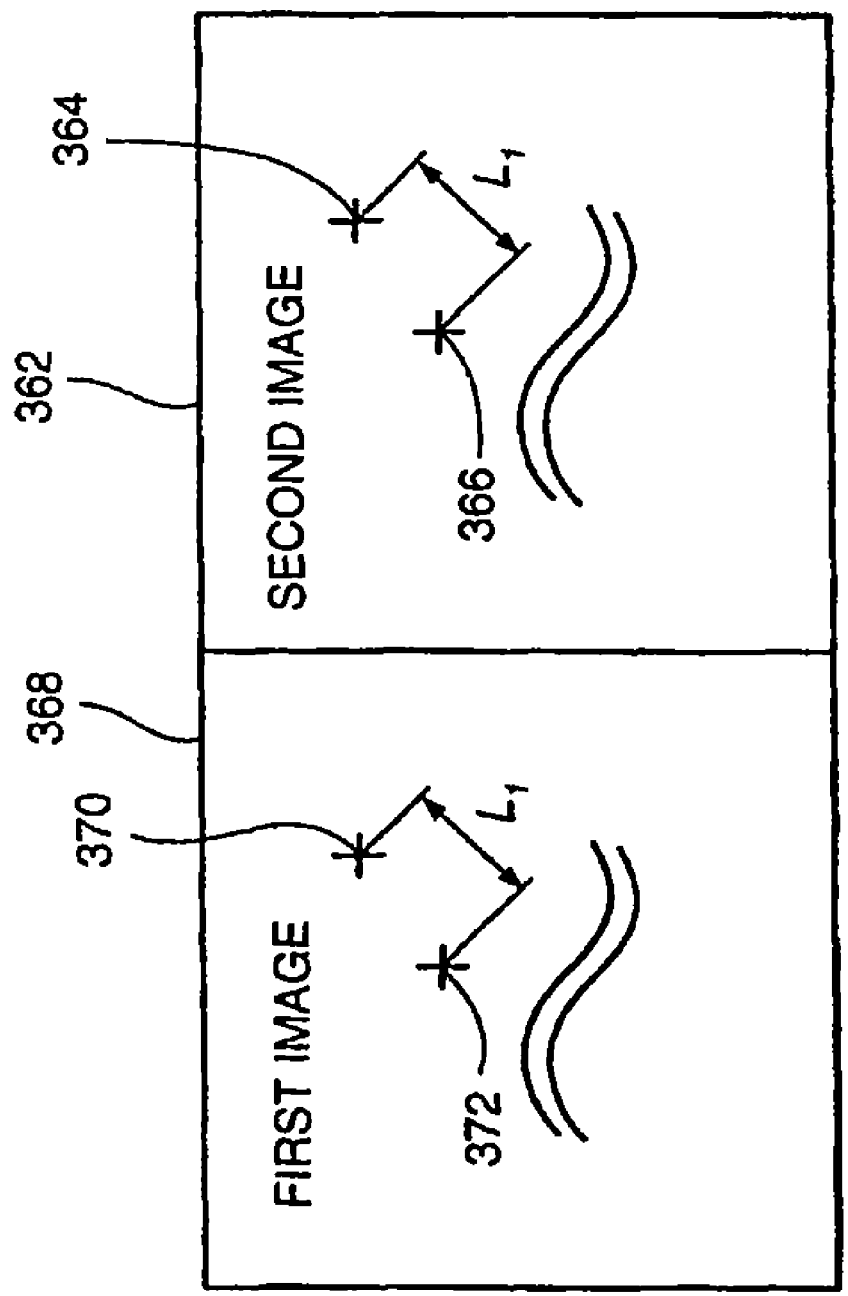
FIG. 3D is a schematic illustration of the first image of FIG. 3B, corrected according to the scale of the second image of FIG. 3C.

Reference is now made to FIGS. 3A, 3B, 3C and 3D. FIG. 3A, is a schematic illustration of two body position and orientation detectors arranged on the body of a patient, to determine the scale factor of an image, according to a further embodiment of the disclosed technique. FIG. 3B is a schematic illustration of a first image of the body of the patient, acquired by a first imager, similar to the first imager of FIG. 1A. FIG. 3C is a schematic illustration of a second image of the body of the patient, acquired by a second imager similar to the second imager of FIG. 1A, wherein the scale of the second image is different from the scale of the first image of FIG. 3B. FIG. 3D is a schematic illustration of the first image of FIG. 3B, corrected according to the scale of the second image of FIG. 3C.

Body position and orientation detectors 350 and 352 are attached to a body 354 of a patient (not shown). Each of body position and orientation detectors 350 and 352 is attached to body 354, in a way similar to the way body position and orientation detector 130 (FIG. 1A) is attached to the body of patient 132. Body position and orientation detectors 350 and 352 are incorporated with a system, such as system 100 (FIG. 1A). Hence, body position and orientation detectors 350 and 352 can be coupled with a first MPS similar to first MPS 102 (FIG. 1B), during image acquisition and with a second MPS similar to second MPS 110 (FIG. 1C), while a medical operation is performed on the patient.

A registering module similar to registering module 112 (FIG. 1C) with which a second imager similar to second imager 108 is coupled, is not aware of the scale factor of the first image and of the second image, produced by the first imager and the second imager, respectively. The distance between body position and orientation detectors 350 and 352 is designated by the letter L.

With reference to FIG. 3B, a first imager similar to first imager 104 (FIG. 1B), produces a first image 356 of an organ (not shown) of body 354, in a display (not shown). Body position and orientation detectors 350 and 352 are represented by two marks 358 and 360, respectively in the display and the distance between marks 358 and 360 is designated by $L_1$.

With reference to FIG. 3C, a second imager similar to second imager 108 (FIG. 1C), produces a second image 362 of the organ in the display. Body position and orientation detectors 350 and 352 are represented by two marks 364 and 366, respectively in the display and the distance between marks 364 and 366 is designated by $L_2$.

In the example set forth in FIGS. 3B and 3C, the scale of first image 356 is twice that of second image 362 (i.e., $L_1=2 L_2$). In order to provide the correct impression of the first image and the second image to a viewer (not shown), the first image and the second image have to be displayed at substantially the same scale.

With reference to FIG. 3D, the registering module scales down first image 356 by 200%, thereby producing another first image 368. Body position and orientation detectors 350 and 352 are represented by two marks 370 and 372, respectively in the display and the distance between marks 370 and 372 is $L_1$ (i.e., the same as that of marks 364 and 366). Thus, first image 368 and second image 362 are displayed side by side, at substantially the same scale.

Figure 4:
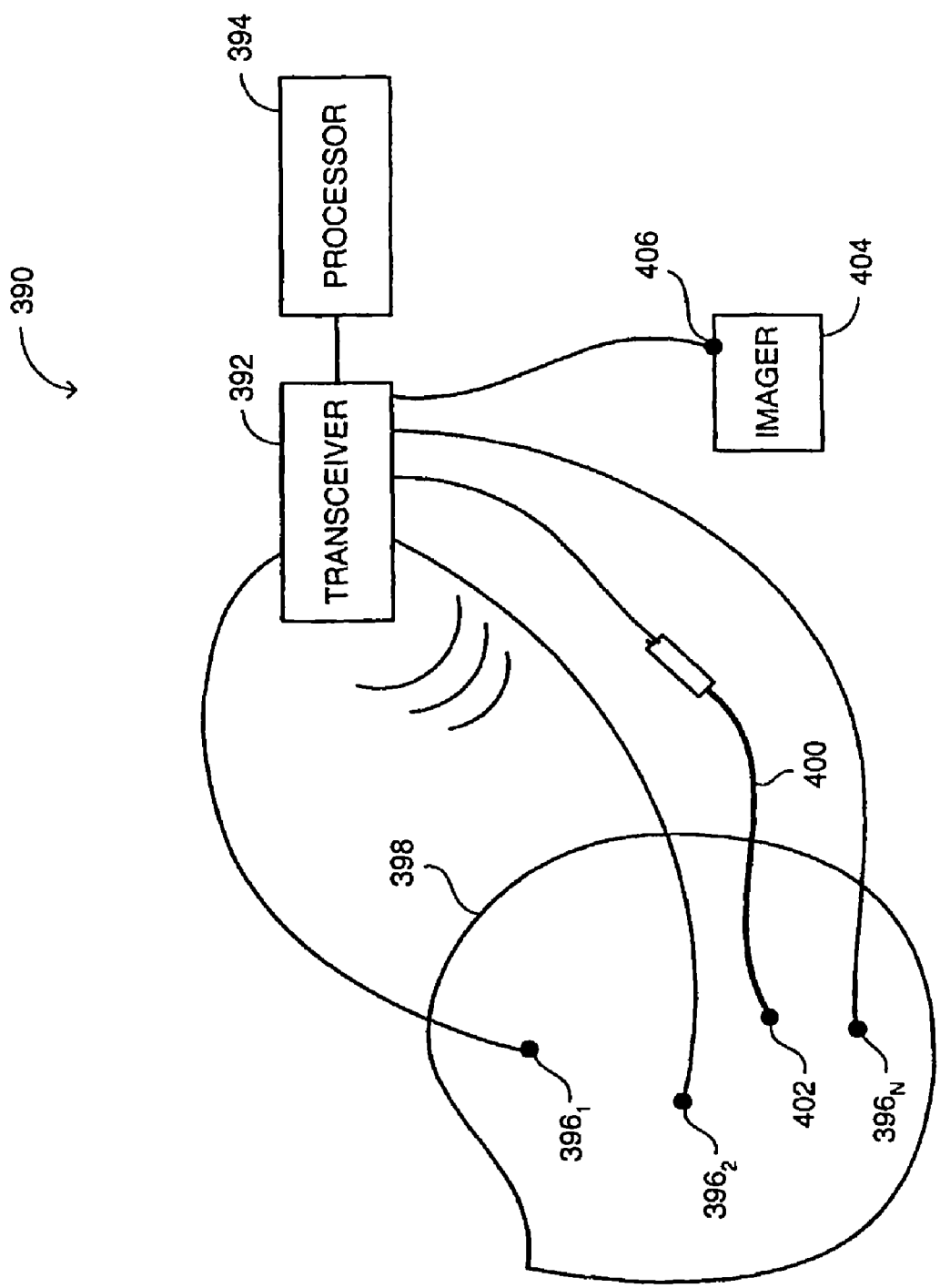
FIG. 4 is a schematic illustration of a portion of the system of FIG. 1A, in which each of the first MPS and the second MPS is replaced by a coordinate determining unit, constructed and operative according to another embodiment of the disclosed technique.

Reference is now made to FIG. 4, which is a schematic illustration of a portion of the system of FIG. 1A, in which each of the first MPS and the second MPS is replaced by a coordinate determining unit, generally referenced 390, constructed and operative according to another embodiment of the disclosed technique. Coordinate determining unit (CDU) 390 includes a transceiver 392, a processor 394 and a plurality of sensing units $396_1$, $396_2$ and $396_N$.

In a system similar to system 100 (FIG. 1A), first MPS 102 can be replaced with a first CDU and second MPS 110 can be replaced by a second CDU. The first CDU includes a first transceiver and a first processor, and the second CDU includes a second transceiver and a second processor. The first CDU is associated with a first coordinate system similar to coordinate system I (FIG. 1B) and the second CDU is associated with a second coordinate system similar to coordinate system I (FIG. 1C).

The first processor is coupled with the first transceiver and with a first imager similar to first imager 104 (FIG. 1A), and the second processor is coupled with a second imager similar to second imager 108 and with a registering module similar to registering module 112. In an image acquisition stage similar to the one illustrated herein above in FIG. 1B, sensing units $396_1$, $396_2$ and $396_N$ are coupled with the first transceiver. In an image registration stage similar to the one illustrated herein above in FIG. 1C, sensing units $396_1$, $396_2$ and $396_N$ are coupled with the second transceiver.

Each of sensing units $396_1$, $396_2$ and $396_N$ is attached to the body 398 of a patient (not shown), similar to the way body position and orientation detector 130 (FIG. 1B), is attached to the body of patient 132. Each of sensing units $396_1$, $396_2$ and $396_N$ includes a location detector and an orientation detector. The location detector can be an electromagnetic coil, sonar sensor (e.g., ultrasound), and the like.

The orientation detector can be a miniature gyroscope, and the like. This type of gyroscope includes an oscillating chip mounted element and a plurality of sensors and it is sold under the trademark GyroChip™, by BEI Systron Donner Inertial Division, Germany. The oscillating element oscillates by a quartz element and the sensors produce a current proportional to rotation of the oscillating element about an axis of the sensors. Transceiver 392 is coupled with processor 394 and with sensing units $396_1$, $396_2$ and $396_N$.

Transceiver 392 transmits a signal (e.g., electromagnetic or acoustic), toward the location detector of each of sensing units $396_1$, $396_2$ and $396_N$. The location detector of each of sensing units $396_1$, $396_2$ and $396_N$ transmits a signal respective of the location thereof, to transceiver 392, via a respective wiring. The orientation detector of each of sensing units $396_1$, $396_2$ and $396_N$ transmits a signal respective of the orientation thereof, to transceiver 392, via another respective wiring. Processor 394 determines the position and orientation of body 398 according to the signals received by transceiver 392.

Additionally, a medical intervention device 400 can be inserted into body 398 and a sensing unit 402 can be attached to a distal end of medical intervention device 400 and sensing unit 402 can be coupled with transceiver 392. Sensing unit 402 is similar to each of sensing units $396_1$, $396_2$ and $396_N$. In this case, processor 394 can determine the position and orientation of the distal end of medical intervention device 400, according to signals received from sensing unit 402.

Further additionally, an imager 404, such as an ultrasound transducer, OCT element, MRI element, thermography element, angiography element, and the like, can be employed to acquire an image of body 398. In this case, a sensing unit 406 is attached to imager 404 and sensing unit 406 is coupled with transceiver 392. Sensing unit 406 is similar to each of sensing units $396_1$, $396_2$ and $396_N$. Processor 394 determines the position and orientation of imager 404 according to signals received from sensing unit 406 and sensing units 396₁, 396₂ and 396_N, by transceiver 392.

Figure 5:
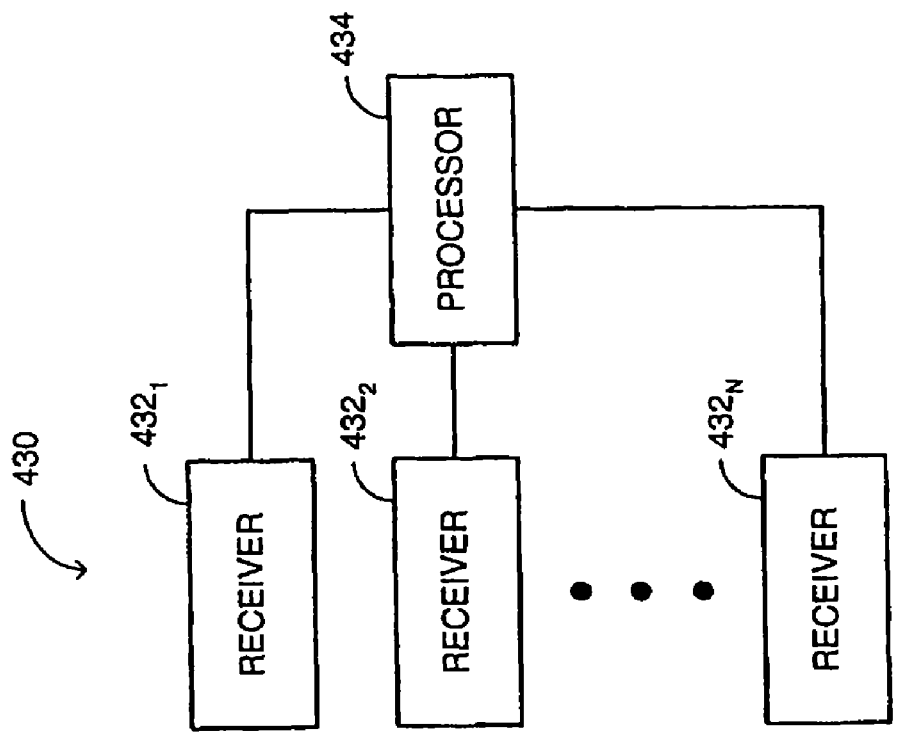
FIG. 5 is a schematic illustration of a portion of the system of FIG. 1A, in which each of the first MPS and the second MPS is replaced by a coordinate determining unit, constructed and operative according to a further embodiment of the disclosed technique.
Figure 5:
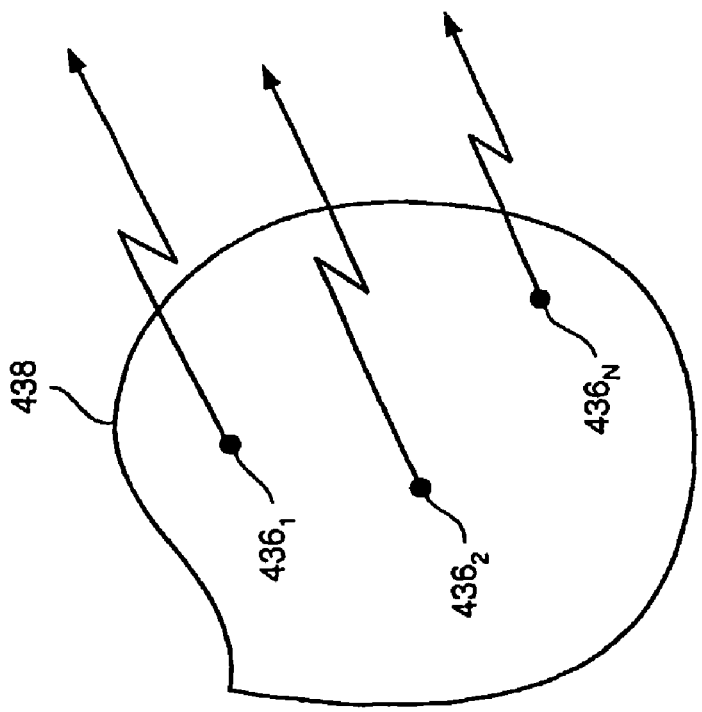

Reference is now made to FIG. 5, which is a schematic illustration of a portion of the system of FIG. 1A, in which each of the first MPS and the second MPS is replaced by a coordinate determining unit, generally referenced 430, constructed and operative according to a further embodiment of the disclosed technique. Coordinate determining unit 430 includes a plurality of receivers 432₁, 432₂ and 432_N, a processor 434 and a plurality of transmitters 436₁, 436₂ and 436_N. Transmitters 436₁, 436₂ and 436_N are attached to a body 438 of a patient (not shown), similar to the way body position and orientation detector 130 (FIG. 1B), is attached to the body of patient 132. Receivers 432₁, 432₂ and 432_N, are coupled with processor 434.

Each of transmitters 436₁, 436₂ and 436_N transmits a signal to receivers 432₁, 432₂ and 432_N. This signal can be electromagnetic (e.g., radio frequency or radio pulses), optic (e.g., infrared), acoustic (e.g., ultrasound), and the like. Processor 434 determines the position and orientation of body 438 according to signals received from receivers 432₁, 432₂ and 432_N and by employing a triangulation method.

Figure 6:
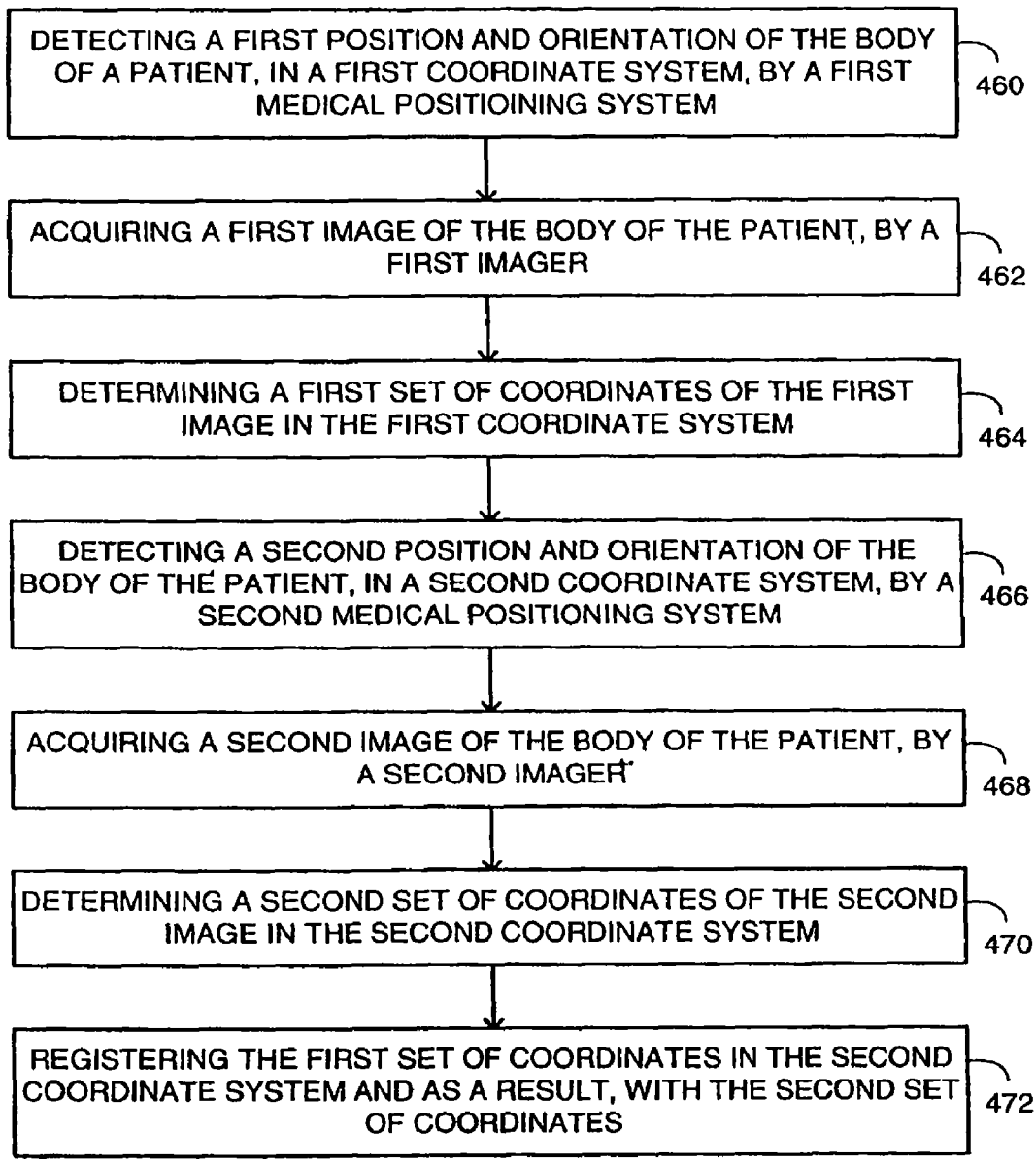
FIG. 6 is a schematic illustration of a method for operating the system of FIG. 1A, operative according to another embodiment of the disclosed technique.

Reference is now made to FIG. 6, which is a schematic illustration of a method for operating the system of FIG. 1A, operative according to another embodiment of the disclosed technique. In procedure 460, a first position and orientation of the body of a patient is detected in a first coordinate system, by a first medical positioning system. With reference to FIG. 1B, first MPS 102 determines the position and orientation of the body of patient 132 in coordinate system I, according to a signal received from body position and orientation detector 130. It is noted that first MPS 102 and body position and orientation detector 130, can be replaced by either coordinate determining unit 390 (FIG. 4) or coordinate determining unit 430 (FIG. 5).

In procedure 462, a first image of the body of the patient is acquired by a first imager. With reference to FIG. 1B, first imager 104 acquires first image 134 of the body of patient 132.

In procedure 464, a first set of coordinates of the first image is determined in the first coordinate system. With reference to FIG. 1B, first imager 104 determines the set of coordinates of first image 134 in coordinate system I, and stores in image database 106, this set of coordinates together with the coordinates of body position and orientation detector 130 which were detected in procedure 460.

In procedure 466, a second position and orientation of the body of the patient is detected in a second coordinate system, by a second medical positioning system. With reference to FIG. 1C, second MPS 110 determines the position and orientation of body position and orientation detector 130 in coordinate system II, according to a signal received from body position and orientation detector 130. It is noted that second MPS 110 and body position and orientation detector 130, can be replaced by either coordinate determining unit 390 (FIG. 4) or coordinate determining unit 430 (FIG. 5).

In procedure 468, a second image of the body of the patient is acquired by a second imager. With reference to FIG. 1C, second imager 108 acquires second image 150 of the body of patient 132.

In procedure 470, a second set of coordinates of the second image is determined in a second coordinate system. With reference to FIG. 1C, second imager 108 determines the set of coordinates of second image 150 in coordinate system II and associates this set of coordinates with the coordinates of body position and orientation detector 130, which were detected in procedure 466.

In procedure 472, the first set of coordinates is registered in the second coordinate system and as a result, with the second set of coordinates. With reference to FIG. 1C, registering module 112 retrieves the data respective of the set of coordinates of first image 134 in coordinate system I and the coordinates of body position and orientation detector 130 in coordinate system I, from image database 106. Registering module 112 receives a signal respective of the set of coordinates of second image 150 in coordinate system II and the coordinates of body position and orientation detector 130 in coordinate system II, from second imager 108. Registering module 112 registers first image 134 in coordinate system II and as a result, with second image 150, by registering the coordinates of body position and orientation detector 130 in coordinate system I, with the coordinates of body position and orientation detector 130 in coordinate system II.

Registering module 112 also receives a signal from second MPS 110, respective of the position and orientation of the distal end of medical intervention device 152. Registering module 112 superimposes real time visual representation 158 of the distal end of medical intervention device 152 on first image 134. First image 134 and second image 150 can be displayed side by side in a display, or superimposed on one another.

According to another aspect of the disclosed technique, a selected position and orientation of a selected tissue of the body of a patient, is recurrently obtained relative to a therapeutic device, by a medical positioning system. The selected position and orientation, which is the one which is suitable for the selected tissue to be effectively medically treated by the therapeutic device, is detected once during the first treatment, and stored in a database. At the start of every subsequent treatment, the portion of the body of the patient is re-positioned such that the currently detected position and orientation of the detector substantially matches the selected position and orientation.

The term "selected tissue" herein below, refers to a tissue of the body of a patient, either internal (i.e., internal organs of the body) or external (e.g., skin, nails, or cornea) which is to be operated on (e.g., by irradiation, or by surgery). The selected tissue can be a tumoral part of an organ of the body, such as hyperplasia (i.e., a tissue having an excessive number of cells), neoplasia (formation of new tissue), benign tumor, malignant tumor, carcinoma, and the like (in case of irradiation), or a non-tumoral part of an organ of the body, such as brain, liver, lungs, kidneys, and the like (in case of surgery).

Figure 7:
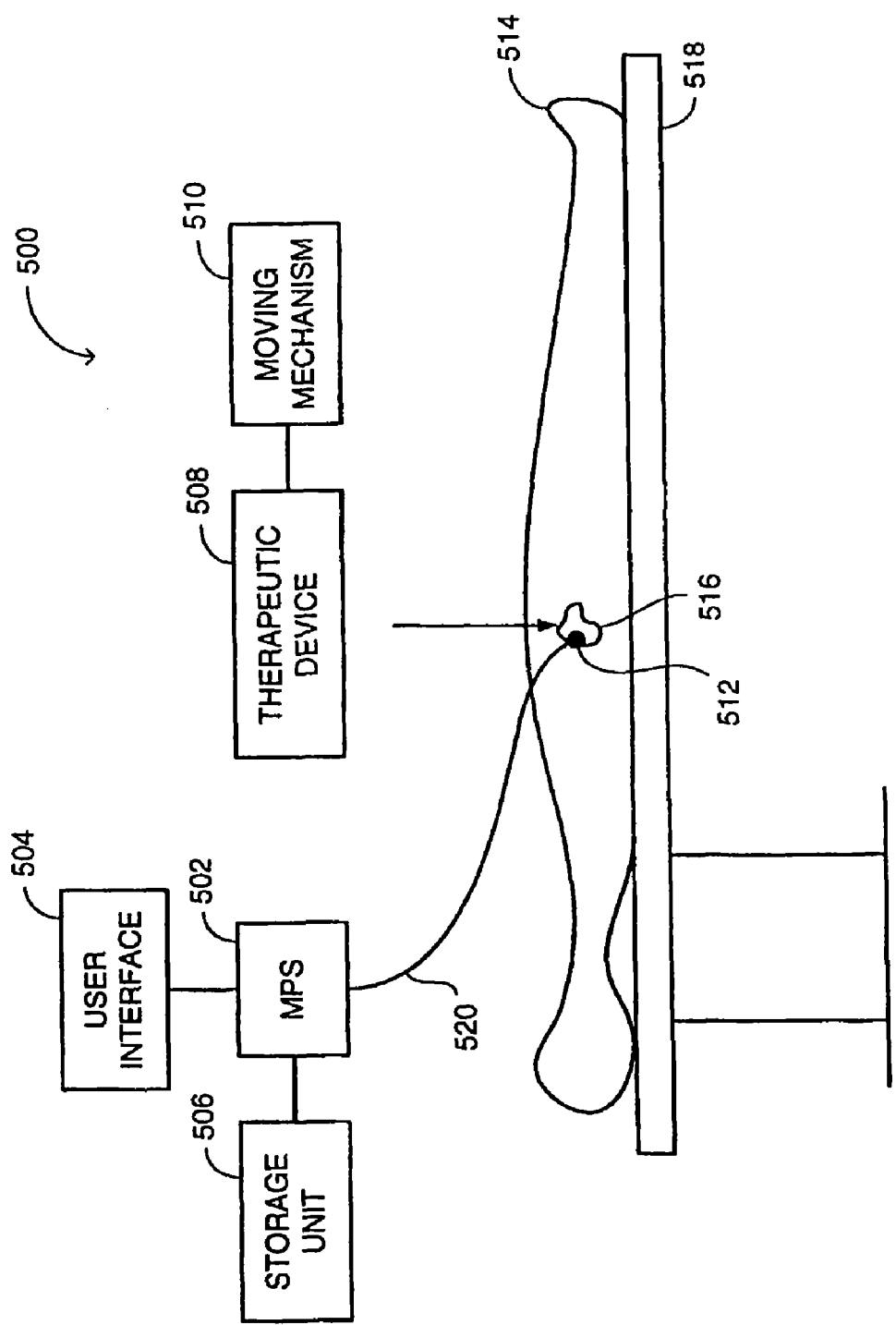
FIG. 7 is a schematic illustration of a system for medically treating a selected tissue of a patient during a plurality of different treatment sessions, constructed and operative according to a further embodiment of the disclosed technique.

Reference is now made to FIG. 7, which is a schematic illustration of a system for medically treating a selected tissue of a patient during a plurality of different treatment sessions, generally referenced 500, constructed and operative according to a further embodiment of the disclosed technique. System 540 includes an MPS 502, a positioning user interface 504, a storage unit 506, a therapeutic device 508 and a moving mechanism 510.

MPS 502 is similar to first MPS 102 (FIG. 1A), as described herein above. Positioning user interface 504 is a tactile, audio, visual, kinesthetic user interface, and the like. Storage unit 506 is a magnetic memory unit, optical memory unit, integrated circuit, and the like, such as hard disk, floppy diskette, compact disk, magnetic tape, flash memory, random access memory, read only memory, and the like.

Therapeutic device 508 is a tissue treating device such as a linear accelerator, local robotic surgical device, remote tele-surgical device, and the like. A linear accelerator is a device which produces high energy X-rays and electron beams, and bombards the selected tissue located at a predetermined point or volume in space, from different directions. A local robotic surgical device is a device which is operated by the clinical staff from a substantially close distance from the patient, such as from a control room in the same hospital. A remote telesurgical device is a device which is operated by the clinical staff from a remote location, via a network, such as local area network (LAN), wide area network (WAN) (e.g., the Internet), metropolitan area network (MAN), and the like. Moving mechanism 510 is coupled with therapeutic device 508, in order to move therapeutic device 508 to different orientations and enable therapeutic device 508 to bombard the selected tissue from different directions. In general, a moving mechanism is adapted to move either the therapeutic device or the patient or both, relative to one another.

Therapeutic device 508 can for example, be in form of a C-arm which is free to rotate about one axis, thus having one degree of freedom. Alternatively, therapeutic device 508 can have more than one degrees of freedom. In the example set forth in FIG. 7, therapeutic device 508 is a linear accelerator. Moving mechanism 510 is an electromechanical element (e.g., rotary or linear electric motor including power transmission elements, such gears, pulleys and belts), electromagnetic element (e.g., an electromagnetic coil and a moving core, and vice versa), hydraulic element, pneumatic element, and the like.

A detector 512 is implanted in the body of a patient 514, at a selected location associated with a selected tissue 516 located within the body and it is fixed at this location, during the period that patient 514 is under medical treatment. Detector 512 is similar to body position and orientation detector 130 (FIG. 1B), as described herein above. Detector 512 can be implanted in the body, either invasively (i.e., by performing an incision), or non-invasively (e.g., with the aid of a needle—not shown, or a catheter—not shown). In case a catheter is employed, detector 512 is coupled with a distal end of the catheter, and detector 512 is inserted into the body with the aid of the catheter. Detector 512 is left in the body for the entire treatment period. In the example set forth in FIG. 7, detector 512 is implanted within selected tissue 516.

Detector 512 is coupled with MPS 502 by a wiring 520 and a quick disconnect plug (not shown). Detector 512 can be plugged into MPS 502 prior to the start of every treatment session and disconnected after the session. MPS 502 is coupled with positioning user interface 504. Alternatively, the detector is coupled with the MPS wirelessly.

During the first treatment session, the clinical staff (not shown) positions a portion of the body of patient 514 to a position and orientation (i.e., therapeutic position and orientation), such that selected tissue 516 is located at a position and orientation suitable for therapeutic device 508 to effectively treat selected tissue 516. At this point, MPS 502 detects the position and orientation of detector 512 (i.e., an initial position and orientation) and the clinical staff stores this initial position and orientation in storage unit 506, via positioning user interface 504.

Prior to the start of every subsequent treatment session, the clinical staff couples detector 512 with MPS 502. Patient 514 lies on an operating table 518 and the clinical staff positions a portion of the body of patient 514 at the therapeutic position and orientation, such that the position and orientation of detector 512 is substantially identical with the stored position and orientation. At this time, this portion of the body of patient 514 is in the same position and orientation as in the first treatment session.

It is noted that system 500 enables the clinical staff to repeatedly reposition the body of patient 514 at each subsequent treatment session, at the same position and orientation as in the first treatment session. It is further noted that operating table 518 can be replaced by another confinement device, adapted to secure selected tissues in place, during a treatment session.

The clinical staff can determine the therapeutic position and orientation of the body, for example, by comparing the position and orientation of detector 512 detected in a subsequent treatment session (i.e., an intermediate position and orientation), with the one detected during the first treatment session (i.e., the initial position and orientation). For this purpose, positioning user interface 504 produces representations of these two positions and orientations, for example, visually, acoustically, kinesthetically, and the like. After positioning the portion of the body of patient 514 at the therapeutic position and orientation, and maintaining this therapeutic position and orientation, the clinical staff directs therapeutic device 508, to automatically treat selected tissue 516 (e.g., when using a linear accelerator, to irradiate the selected tissue from different directions).

A controller (not shown) can be coupled with therapeutic device 508 and with moving mechanism 510. The system can further include another a therapeutic device user interface (not shown), coupled with the controller. The controller can be programmed to control moving mechanism 510 to move therapeutic device 508, in order to medically treat selected tissue 516 from these directions. This program is fixed and invariable and is permanently stored in the controller. Alternatively, the clinical staff can alter the program by entering the respective parameters to the controller, via the therapeutic device user interface.

The controller is further coupled with MPS 502. MPS 502 detects the position and orientation of detector 512 and provides a respective signal to the controller. The controller directs moving mechanism 510 to move therapeutic device 508 according to the signal received from MPS 502, in a closed loop (i.e., according to feedback from MPS 502). In this manner, the controller directs moving mechanism 510 to change the position and orientation of therapeutic device 508, according to changes in the position and orientation of selected tissue 516 (i.e., movements of the body of patient 514).

Thus, system 500 enables the clinical staff to treat patient 514 while patient 514 is in an unrestrained position and free to move. The quality of treatment in the unrestrained position is substantially the same than in the case where the body of patient 514 is restrained and therapeutic device 508 does not follow the movements of patient 514 in a closed loop.

Further alternatively, the clinical staff enters a set of coordinates respective of the boundary of the selected tissue to the controller, via the therapeutic device user interface. The controller controls the moving mechanism to move the therapeutic device according to the entered set of coordinates, in order to automatically medically treat the selected tissue. The entered set of coordinates can be either discrete (i.e., numerical values), or volumetric (e.g., radius of a sphere from a reference point, height, width and depth of a cube, or radius of the base of a cylinder and the height thereof).

Further alternatively, the moving mechanism is coupled with the operating table and the controller is coupled with the moving mechanism and with the therapeutic device user interface. The clinical staff enters a set of coordinates respective of the boundary of the selected tissue to the controller, via the therapeutic device user interface. The controller controls the moving mechanism to move the operating table according to the entered set of coordinates, in order to allow the therapeutic device to medically treat the selected tissue.

Further alternatively, the moving mechanism is coupled both with the therapeutic device and the operating table. In any case, the moving mechanism provides movement of the selected tissue relative to the therapeutic device, in order to allow the therapeutic device to medically treat the selected tissue.

Alternatively, a comparator (not shown) is coupled with MPS 502, storage unit 506 and with positioning user interface 504, wherein the comparator compares the position and orientation of the detector at a subsequent treatment session, with the one detected during the first treatment session. The comparator provides a signal to positioning user interface 504, when the comparator determines that the stored position and orientation is substantially identical to the currently detected position and orientation.

Positioning user interface 504 produces an indication, such as an audible sound, a visual cue, a tactile indication, and the like, according to the signal received from the comparator. The clinical staff determines according to this indication, that the portion of the body of patient 514 is located at a position and orientation, suitable for selected tissue 516 to be medically treated by the therapeutic device. Further alternatively, the detector can be implanted at a selected location so close to the selected tissue, that the clinical staff can assure that when the detector is located at the selected position and orientation, the position and orientation of the selected tissue is suitable for medical treatment.

Figure 8:
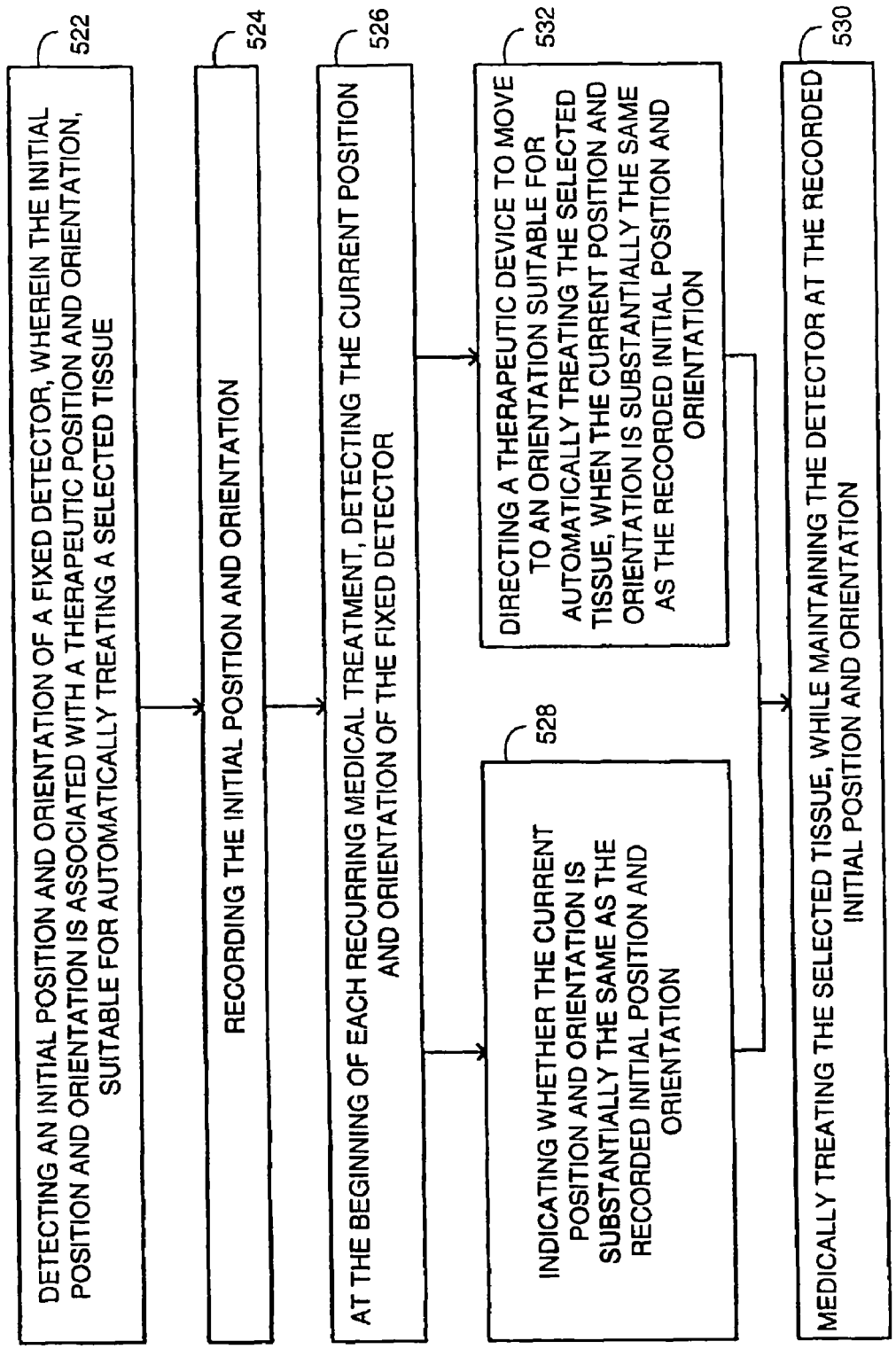
FIG. 8 is a schematic illustration of a method for operating the system of FIG. 7, operative according to another embodiment of the disclosed technique.

Reference is now made to FIG. 8, which is a schematic illustration of a method for operating the system of FIG. 7, operative according to another embodiment of the disclosed technique. In procedure 522, an initial position and orientation of a fixed detector is detected, wherein the initial position and orientation is associated with a therapeutic position and orientation, suitable for automatically treating a selected tissue of the body of a patient. With reference to FIG. 7, MPS 502 detects the position and orientation of detector 512, when detector 512 is at a position and orientation (i.e., a therapeutic position and orientation), suitable for therapeutic device 508 to automatically treat selected tissue 516.

Detector 512 is previously implanted by the clinical staff, within selected tissue 516. Alternatively, the position and orientation detector can be implanted at a location which is substantially close to the selected tissue (i.e., the spatial relations between the position and orientation detector and the selected tissue should remain unchanged at all times), so that the clinical staff can assure that this position and orientation, determines a position and orientation for the selected tissue to be effectively treated by the therapeutic device.

In procedure 524, the initial position and orientation is recorded. With reference to FIG. 7, MPS 502 stores in storage unit 506, the position and orientation of detector 512, as detected in procedure 522. Alternatively, the clinical staff stores a set of coordinates respective of the position and orientation of detector 512 corresponding with the therapeutic position and orientation, via positioning user interface 504. This set of coordinates can be determined at the treatment planning stage, for example according to an image of the selected tissue.

In procedure 526, the current position and orientation of the fixed detector is detected, at the beginning of each recurring medical treatment. With reference to FIG. 7, during each subsequent treatment session and before the medical treatment, MPS 502 detects the position and orientation of detector 512, while the clinical staff moves a portion of the body of patient 514 which includes selected tissue 516. Following procedure 526 the method can proceed either to procedure 528 or to procedure 532.

In procedure 528, it is indicated whether the current position and orientation is substantially the same as the recorded initial position and orientation. With reference to FIG. 7, as the clinical staff moves the portion of the body of patient 514 which includes selected tissue 516, positioning user interface 504 indicates whether the current position and orientation of detector 512 is substantially the same as the one which was recorded in procedure 524. Positioning user interface 504 produces indications respective of the current position and orientation of detector 512 and the recorded position and orientation (e.g., visually), and the clinical staff moves patient 514 accordingly. Alternatively, positioning user interface 504 notifies (e.g., audibly) the clinical staff that the current position and orientation of detector 512 substantially matches the initial position and orientation as recorded in procedure 524.

In procedure 530, the selected tissue is medically treated, while maintaining the detector at the recorded initial position and orientation. With reference to FIG. 7, therapeutic device 508 medically treats selected tissue 516 (e.g., irradiating selected tissue 516 from different directions), while the clinical staff maintains detector 512, and thus selected tissue 516, at the position and orientation which was recorded in procedure 524.

In procedure 532, a therapeutic device is directed to an orientation suitable for automatically treating the selected tissue, when the current position and orientation is substantially the same as the recorded initial position and orientation. In this case, in a system similar to system 500 (FIG. 7), the MPS is coupled with the therapeutic device. Whenever the position and orientation of the detector and thus of the selected tissue is substantially the same as that of the recorded initial position and orientation, the MPS directs the therapeutic device to automatically treat the selected tissue.

According to a further aspect of the disclosed technique, one of the coordinate systems is that of an automated medical therapeutic device. In the following example, the automated medical therapeutic system is a linear accelerator, used for irradiating a selected point by irradiating a plurality of axes which cross it. Here, a position and orientation detector is placed within the body of the patient, at a selected location associated with a selected tissue. The clinical staff determines the position and orientation of a portion of the body at the planning stage and records the position and orientation of the detector. At the radiation treatment stage, a registering module registers the position and orientation of the detector at the radiation treatment stage with the one determined during the planning stage. The clinical staff, then repositions the portion of the body, such that the position and orientation of the detector is substantially the same as the one determined at the planning stage and directs the therapeutic device to irradiate the selected tissue.

Figure 9A:
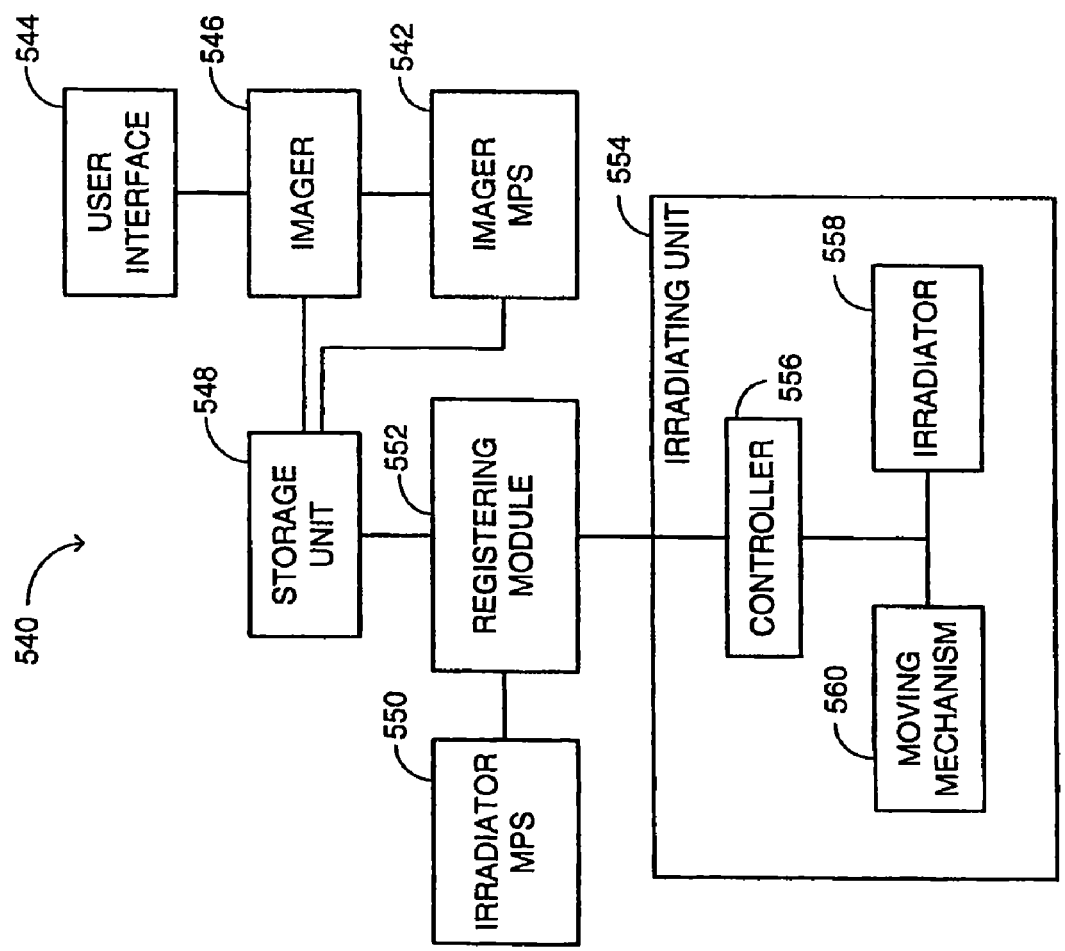
FIG. 9A is a schematic illustration of a system for registering the boundary of a selected tissue defined in the coordinate system of an imager, with the coordinate system of a therapeutic device, constructed and operative according to a further embodiment of the disclosed technique.
Figure 9B:
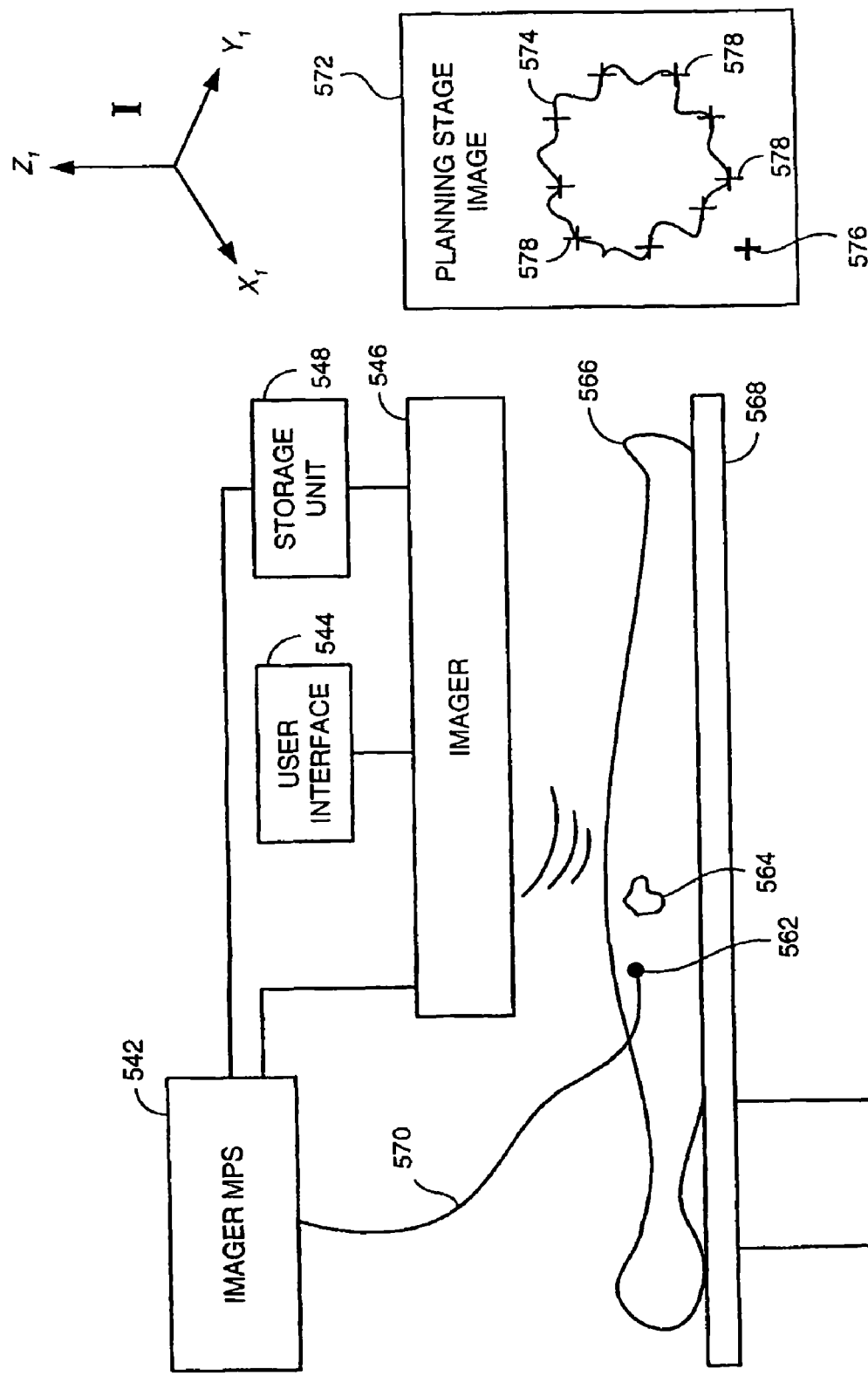
FIG. 9B is a schematic illustration of an irradiation planning portion of the system of FIG. 9A.
Figure 9C:
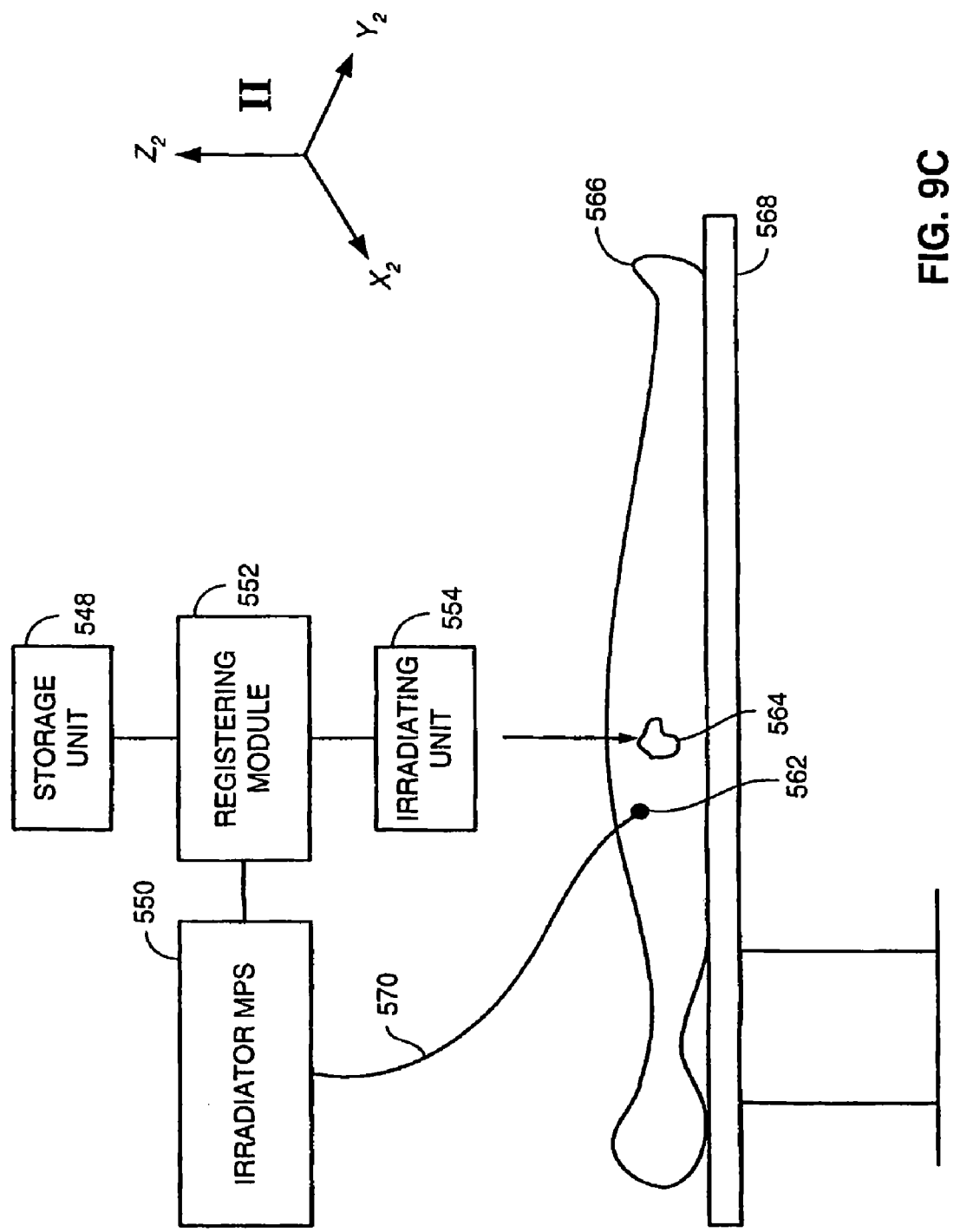
FIG. 9C is a schematic illustration of a radiation treatment portion of the system of FIG. 9A.

Reference is now made to FIGS. 9A, 9B and 9C. FIG. 9A is a schematic illustration of a system for registering the boundary of a selected tissue defined in the coordinate system of an imager, with the coordinate system of a therapeutic device, generally referenced 540, constructed and operative according to a further embodiment of the disclosed technique. FIG. 9B is a schematic illustration of an irradiation planning portion of the system of FIG. 9A. FIG. 9C is a schematic illustration of a radiation treatment portion of the system of FIG. 9A.

With reference to FIG. 9A, system 540 includes an imager MPS 542, a user interface 544, an imager 546, a storage unit 548, an irradiator MPS 550, a registering module 552 and an irradiating unit 554. Irradiating unit 554 includes a controller 556, an irradiator 558 and a moving mechanism 560. Imager 546 is coupled with imager MPS 542, user interface 544 and with storage unit 548. Storage unit 548 is coupled with imager MPS 542. Registering module 552 is coupled with storage unit 548, irradiator MPS 550 and with irradiating unit 554. Controller 556 is coupled with irradiator 558 and with moving mechanism 560.

Imager MPS 542, imager 546, irradiator MPS 550 and registering module 552 are similar to first MPS 102 (FIG. 1A), first imager 104, second MPS 110 and registering module 112, respectively, as described herein above. Imager 546 can be a three-dimensional type imager, such as computer tomography, ultrasound, and the like. Storage unit 548 and moving mechanism 560 are similar to storage unit 506 (FIG. 7) and moving mechanism 510, respectively, as described herein above. User interface 544 is a tactile user interface, audio, visual, and the like, such as a keyboard, mouse, stylus, microphone, display (e.g., touch-screen display), and the like, or a combination thereof. Irradiator 558 is similar to the linear accelerator, as described herein above in connection with therapeutic device 508 (FIG. 7).

With reference to FIG. 9B, imager 546 is coupled with imager MPS 542 and with storage unit 548. Imager MPS 542 is coupled with storage unit 548. A position and orientation detector 562 is placed at a selected location associated with a selected tissue 564 of a patient 566, similar to the way detector 512 (FIG. 7), is placed within the body of patient 514. Alternatively, position and orientation detector 562 can be inserted into the body of patient 566, at the selected location, by employing a body intrusion device (not shown), such as a catheter, needle, and the like. Position and orientation detector 562 is similar to body position and orientation detector 130 (FIG. 1B), as described herein above. Patient 566 lies on an operating table 568.

Imager MPS 542 is associated with an $X_1$, $Y_1$, $Z_1$ coordinate system (i.e., coordinate system I). Imager 546 is calibrated with imager MPS 542, such that the position and orientation of imager 546 is defined relative to coordinate system I. Position and orientation detector 562 provides a signal respective of the position and orientation thereof, to imager MPS 542 via wiring 570 (alternatively, wirelessly). Imager MPS 542 determines the position and orientation of position and orientation detector 562 in coordinate system I, according to the signal received from position and orientation detector 562.

Imager MPS 542 provides a signal respective of the position and orientation of position and orientation detector 562, to imager 546. Imager 546 produces a signal respective of a planning stage image 572 of a tissue image 574 of selected tissue 564 and a detector image 576 of position and orientation detector 562. Planning stage image 572 can be either two-dimensional or three-dimensional. Imager 546 provides this signal to user interface 544 and user interface 544 displays planning stage image 572, according to the received signal. Detector image 576 can be either a real time image of position and orientation detector 562, or a representation thereof. It is noted that it is not necessary for user interface 544 to display detector image 576 and that detector image 576 serves to more clearly describe the disclosed technique.

The clinical staff marks the boundary of tissue image 574 by markings 578, on a selected slice of the images produced by imager 546. Imager 546, then determines a set of coordinates of a three-dimensional image of selected tissue 564, according to the coordinates of markings 526 in the slice. Imager 546 stores this set of coordinates together with the coordinates of position and orientation detector 562, in storage unit 548.

Alternatively, the clinical staff enters a set of coordinates respective of a volume of selected tissue 564 relative to the position and orientation of position and orientation detector 562, to storage unit 548, via user interface 544. The entered set of coordinates can be either discrete (i.e., numerical values), or volumetric (e.g., radius of a sphere from a reference point, height, width and depth of a cube, or radius of the base of a cylinder and the height thereof).

Generally, the planning stage of system 540 as illustrated in FIG. 9B, is performed at a location physically different from the irradiation stage of system 540, as illustrated in FIG. 9C. Hence, wiring 570 is provided with a connector (not shown), in order to disconnect position and orientation detector 562 from imager MPS 542 and connect position and orientation detector 562 to irradiator MPS 550. However, a position and orientation detector can be provided with wireless connections.

With reference to FIG. 9C, registering module 552 is coupled with storage unit 548, irradiator MPS 550 and with irradiating unit 554. Position and orientation detector 562 is coupled with irradiator MPS 550, via wiring 570.

Irradiator MPS 550 is associated with an $X_2$, $Y_2$, $Z_2$ coordinate system (i.e., coordinate system II). Irradiating unit 554 is calibrated with irradiator MPS 550, such that the position and orientation of irradiating unit 554 is defined relative to coordinate system II. Position and orientation detector 562 provides a signal respective of the position and orientation thereof, to irradiator MPS 550. Irradiator MPS 550 determines the position and orientation of position and orientation detector 562 in coordinate system II, according to the signal received from position and orientation detector 562. Irradiator MPS 550 provides a signal respective of the determined position and orientation to registering module 552.

System 540 can be operated either in a manual mode or an automatic mode. In manual mode, moving mechanism 560 can move irradiating unit 558 to automatically irradiate a fixed point in space, from different directions. However, moving mechanism 560 can not move irradiating unit 558 to irradiate points in space, other than the fixed point.

In manual mode, registering module 552 receives data respective of the coordinate system of irradiating unit 554 (i.e., coordinate system II), from irradiating unit 554. Registering module 552, then registers the position and orientation of position and orientation detector 562 in coordinate system I, with the position and orientation of position and orientation detector 562 in coordinate system II. The clinical staff positions the portion of the body of patient 566, such that the position and orientation of position and orientation detector 562 in coordinate system II, is substantially the same as the one determined at the planning stage (i.e., in coordinate system I). Now, selected tissue 564 is located at the fixed point in space, toward which irradiator 558 is set to direct radiations from different directions. At this stage, the clinical staff directs moving mechanism 560 to move irradiator 558, to automatically irradiate selected tissue 564 from different directions.

In automatic mode of operation of system 540, moving mechanism 560 can adjust the position and orientation of irradiator 558 to irradiate substantially any selected point of the body of patient 566. In addition, moving mechanism 560 can move irradiating unit 558, to irradiate the selected point of the body of patient 566, from different directions.

In automatic mode, registering module 552 retrieves from storage unit 548, the data respective of the set of coordinates of the boundary of selected tissue 564 in coordinate system I, and the coordinates of position and orientation detector 562 in coordinate system I. Registering module 552 registers the position and orientation of position and orientation detector 562 in coordinate system I, with the position and orientation of position and orientation detector 562 in coordinate system II.

Registering module 552 provides a signal respective of the set of coordinates of the boundary of selected tissue 564 in coordinate system II and the position and orientation thereof in coordinate system II, to controller 556. Controller 556 determines a position and orientation for irradiator 558, to irradiate the boundary of selected tissue 564, according to the data received from registering module 552, respective of the set of coordinates of selected tissue 564 in coordinate system II and provides a respective signal to moving mechanism 560.

Controller 556 also determines a plurality of orientations for irradiator 558, to irradiate selected tissue 564 from different directions and controller 556 provides a signal respective of these determined orientations to moving mechanism 560. Moving mechanism 560 moves irradiator 558 to the position and orientation determined by controller 556, to irradiate selected tissue 564. Moving mechanism 560 also moves irradiator 558 automatically, to irradiate selected tissue 564 from different directions.

It is noted that in the automatic mode of operation of system 540, there is no need for the clinical staff to manually position the portion of the body of patient 566 relative to irradiator 558. Instead moving mechanism 560 moves irradiator 558 to the appropriate position and orientation.

Controller 556 can be programmed to direct moving mechanism 560 to enable irradiator 558 to irradiate selected tissue 564 from different directions, as described herein above in connection with FIG. 7. In case the scale of coordinate system I and coordinate system II are different, registering module 552 applies the scale factor between these two coordinate systems, while registering the position and orientation of position and orientation detector 562 in coordinate system II, as described herein above in connection with FIG. 1C.

Alternatively, the moving mechanism is coupled with the operating table. In this case, the controller determines a position and orientation of the operating table to move the body of patient 566, such that irradiator 558 can direct radiations toward selected tissue 564. The controller provides a signal respective of the determined orientations to the moving mechanism and the moving mechanism moves the operating table according to the signal received from the controller. In this case too, there is no need for the clinical staff to manually move the portion of the body of patient 566 to a position and orientation appropriate for irradiation, instead the moving mechanism performs this movement.

Alternatively, the moving mechanism is coupled with both the irradiator and the operating table. In any case, the moving mechanism provides relative movement between the selected tissue and the irradiator.

Figure 10:
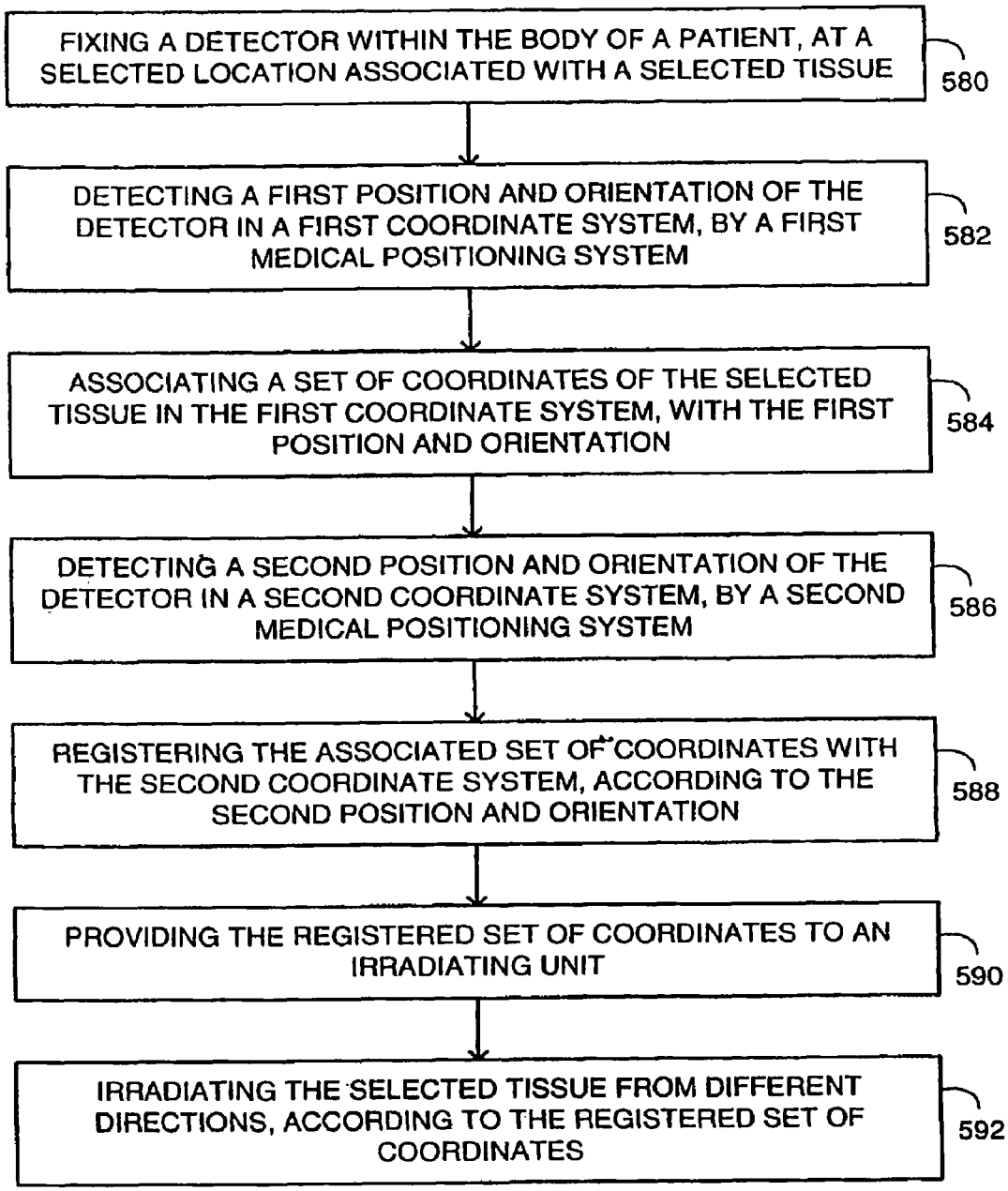
FIG. 10 is a schematic illustration of a method for operating the system of FIG. 9A, operative according to another embodiment of the disclosed technique.

Reference is now made to FIG. 10, which is a schematic illustration of a method for operating the system of FIG. 9A, operative according to another embodiment of the disclosed technique. In procedure 580, a detector is fixed within the body of a patient, at a selected location associated with a selected tissue. With reference to FIG. 9B, position and orientation detector 562 is implanted within the body of patient 522, at the selected location and position and orientation detector 562 is coupled with imager MPS 542, via wiring 570.

In procedure 582, a first position and orientation of the detector in a first coordinate system is detected by a first medical positioning system. With reference to FIG. 9B, imager MPS 542 detects the position and orientation of position and orientation detector 562 in coordinate system I and provides a respective signal to imager 546.

In procedure 584, a set of coordinates of the selected tissue in the first coordinate system, is associated with the first position and orientation. With reference to FIG. 9B, user interface 544 displays a planning stage image 572, which includes tissue image 574 and detector image 576. The clinical staff marks the boundary of tissue image 574 by markings 576, by employing user interface 544. Imager 546 provides the set of coordinates of markings 576 together with the coordinates of position and orientation detector 562, for storage in storage unit 548.

Alternatively, the clinical staff enters a set of coordinates of selected tissue 564 relative to the position and orientation of position and orientation detector 562, via the user interface and stores this set of coordinates together with the coordinates of position and orientation detector 562, in storage unit 548.

In procedure 586, a second position and orientation of the detector in a second coordinate system, is detected by a second medical positioning system. With reference to FIG. 9C, patient 522 is located in an irradiation room, which is usually different than the imaging room illustrated in FIG. 9B and wiring 570 is coupled with irradiator MPS 550. Irradiator MPS 550 detects the position and orientation of position and orientation detector 562 in coordinate system II and provides a respective signal to registering module 552.

In procedure 588, the associated set of coordinates is registered with the second coordinate system, according to the second position and orientation. With reference to FIG. 9C, registering module 552 retrieves the set of coordinates from storage unit 548 and registers them with coordinate system II, according to the position and orientation of position and orientation detector 562 in coordinate system II. Registering module 552 further registers the set of coordinates in coordinate system I, with coordinate system II, according to optional transformation information for transforming data from coordinate system I to coordinate system II (e.g., scaling).

Registering module 552 provides a signal respective of the registered set of coordinates to irradiating unit 554 (procedure 59Q). In procedure 592, the selected tissue is irradiated from different directions, according to the registered set of coordinates. With reference to FIGS. 9A and 9C, controller 556 determines a plurality of orientations for irradiator 558 to irradiate the volume of selected tissue 564 in different directions and controller 556 provides a respective signal to moving mechanism 560. Moving mechanism 560 moves irradiator 558 according to the signal received from controller 556.

Alternatively, the moving mechanism is coupled with the operating table, to allow movement of a portion of the body of the patient relative to the irradiator. Further alternatively, the moving mechanism is coupled both with the operating table and with the irradiator. In all cases, the moving mechanism provides movement of the selected tissue, relative to the irradiator.

According to a further aspect of the disclosed technique, a medical positioning system determines the position and orientation of a detector coupled with a medical intervention device which is inserted into the body of a patient. The medical positioning system directs an imager to move to an orientation, such that the imager can acquire an image of the maximum possible length of a portion of interest of the medical intervention device. This portion of interest, is then displayed in a display.

Figure 11:
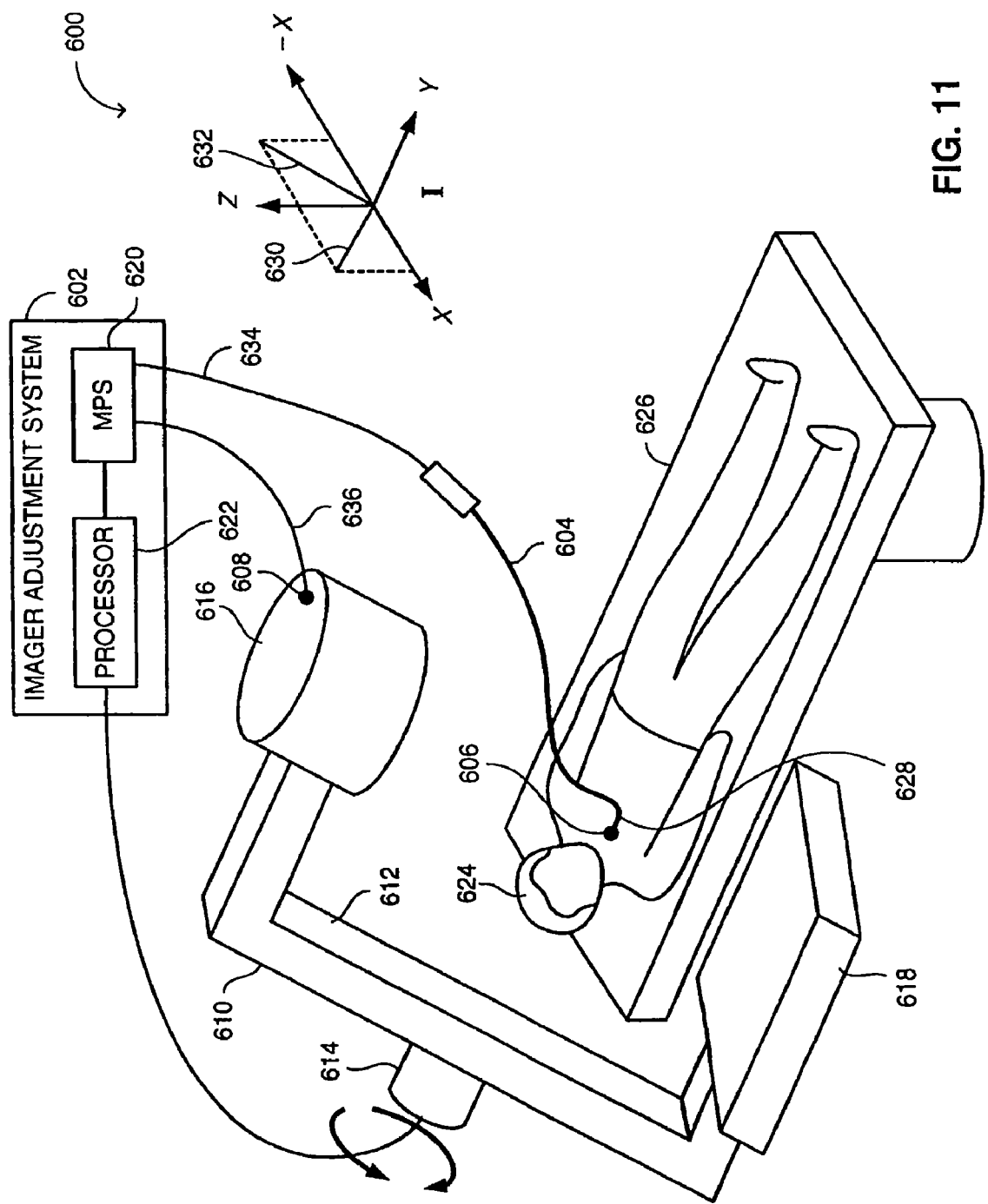
FIG. 11 is a schematic illustration of a system for acquiring an image of a medical intervention device, constructed and operative according to a further embodiment of the disclosed technique.

Reference is now made to FIG. 11, which is a schematic illustration of a system for acquiring an image of a medical intervention device, generally referenced 600, constructed and operative according to a further embodiment of the disclosed technique. System 600 includes an image adjustment system 602, MPS 620, a medical intervention device 604, a device position and orientation detector 606, an imager position and orientation detector 608 and an imager 610. Imager 610 includes a support structure 612, a moving mechanism 614, a radiation generator 616 and a radiation detector 618. Image adjustment system 602 includes an MPS 620 and a processor 622.

Medical intervention device 604 is inserted into the body of a patient 624. Patient 624 lies on an operating table 626. Device position and orientation detector 606 is coupled with medical intervention device 604, at a region of interest of medical intervention device 604, for example at a distal end 628 thereof. Imager position and orientation detector 608 is attached to imager 610. MPS 620 is coupled with device position and orientation detector 606, imager position and orientation detector 608 and with processor 622. Processor 622 is coupled with moving mechanism 614. Imager 610 is a device which acquires an image (not shown) of patient 624 (e.g., fluoroscopy, ultrasound, nuclear magnetic resonance—NMR, optical imaging, nuclear imaging—PET, thermography).

Imager 610 has at least three degrees of freedom. MPS 620 is associated with an X, Y, Z coordinate system (i.e., coordinate system I). Imager 610 is calibrated with MPS 620, such that the position and orientation of imager 610 is defined relative to coordinate system I.

In the example set forth in FIG. 11, imager 610 is an X-ray type imager (known in the art as C-arm imager). Hence, radiation generator 616 and radiation detector 618 are coupled with support structure 612, such that radiation generator 616 is located at one side of patient 624 and radiation detector 618 is located at an opposite side of patient 624. Radiation generator 616 and radiation detector 618 are located on a radiation axis (not shown), wherein the radiation axis crosses the body of patient 624.

Moving mechanism 614 is coupled with support structure 612, thereby enabling support structure 612 to rotate about the Y axis. Moving mechanism 614 rotates support structure 612, thereby changing the orientation of the radiation axis on the X-Z plane and about the Y axis. Moving mechanism 614 is similar to moving mechanism 560 (FIG. 9A), as described herein above. In the example set forth in FIG. 11, device position and orientation detector 606 is located at distal end 628. The orientation of distal end 628 is represented by a vector 632 located on the X-Z plane. In order to obtain an image of the maximum length of distal end 628, the radiation axis has to be aligned along a vector 632 located on the X-Z plane, wherein vector 632 is approximately normal to vector 632.

A transmitter (not shown) transmits an electromagnetic signal to device position and orientation detector 606 and to imager position and orientation detector 608. Device position and orientation detector 606 provides a signal respective of the position and orientation thereof, to MPS 620, via a wiring 634. Likewise, imager position and orientation detector 608 provides a signal respective of the position and orientation of imager 610 to MPS 620, via a wiring 636. Alternatively, each of device position and orientation detector 606 and imager position and orientation detector 608, is coupled with MPS 620 wirelessly.

According to signals received from device position and orientation detector 606 and from imager position and orientation detector 608, MPS 620 detects the position and orientation of device position and orientation detector 606 and of imager position and orientation detector 608, respectively. MPS 620 provides a signal respective of the detected position and orientation of distal end 628 and of the detected position and orientation of imager 610 to processor 622.

Processor 622 determines that distal end 628 points along vector 632 and that the radiation axis has to point along vector 632. Processor 622 determines the direction of vector 632, according to signals received from device position and orientation detector 606 and imager position and orientation detector 608. Processor 622 provides a signal to moving mechanism 614 to move support structure 612 according to the detected position and orientation of imager position and orientation detector 608, such that the radiation axis is oriented along vector 632.

Alternatively, system 600 is devoid of imager position and orientation detector 608. In this case, the coordinates of moving mechanism 614 is synchronized with coordinate system I. Processor 622 determines the direction of vector 632 according to the signal received from device position and orientation detector 606, alone and directs moving mechanism 614 to move support structure 612, such that the radiation axis is oriented along vector 632. Processor 622 moves mechanism 614, without receiving any feedback signal respective of the position and orientation of imager 610 at any time.

Further alternatively, system 600 includes a user interface (not shown) coupled with processor 622, wherein the clinical staff enters data respective of desired orientation ranges of imager 610 to processor 622 via the user interface. Processor 622 provides a signal respective of the orientation data entered by the clinical staff and moving mechanism 614 moves imager 610 according to the signal received from processor 622.

Radiation detector 618 detects the radiation which is produced by radiation generator 616 and which passes through a section of the body of patient 624, and thus produces an image of this section of the body. Radiation detector 618 provides a signal to a display (not shown) and the display displays the image of this section of the body. This image includes an optimal representation of a portion of interest of medical intervention device 604 (i.e., an image of the maximum possible length of distal end 628).

In the example set forth in FIG. 11, the distal end of the medical intervention device points along a direction, such that the imager can rotate toward an orientation, at which the radiation axis of the imager is approximately perpendicular to the direction of the distal end of the medical intervention device.

Thus, if the distal end of the medical intervention device points along a direction, which is not possible to align the radiation axis exactly perpendicular to this direction, then the imager is moved to an orientation at which an image of the longest projection of the distal end (i.e., maximum possible length of the portion of interest), is obtained.

Alternatively or additionally, a moving mechanism (not shown) similar to moving mechanism 614 is coupled with operating table and with the MPS. In this case, the MPS directs the moving mechanism to move the operating table, such that the imager can acquire an image which includes an optimal representation of a portion of interest of the medical intervention device.

Figure 12:
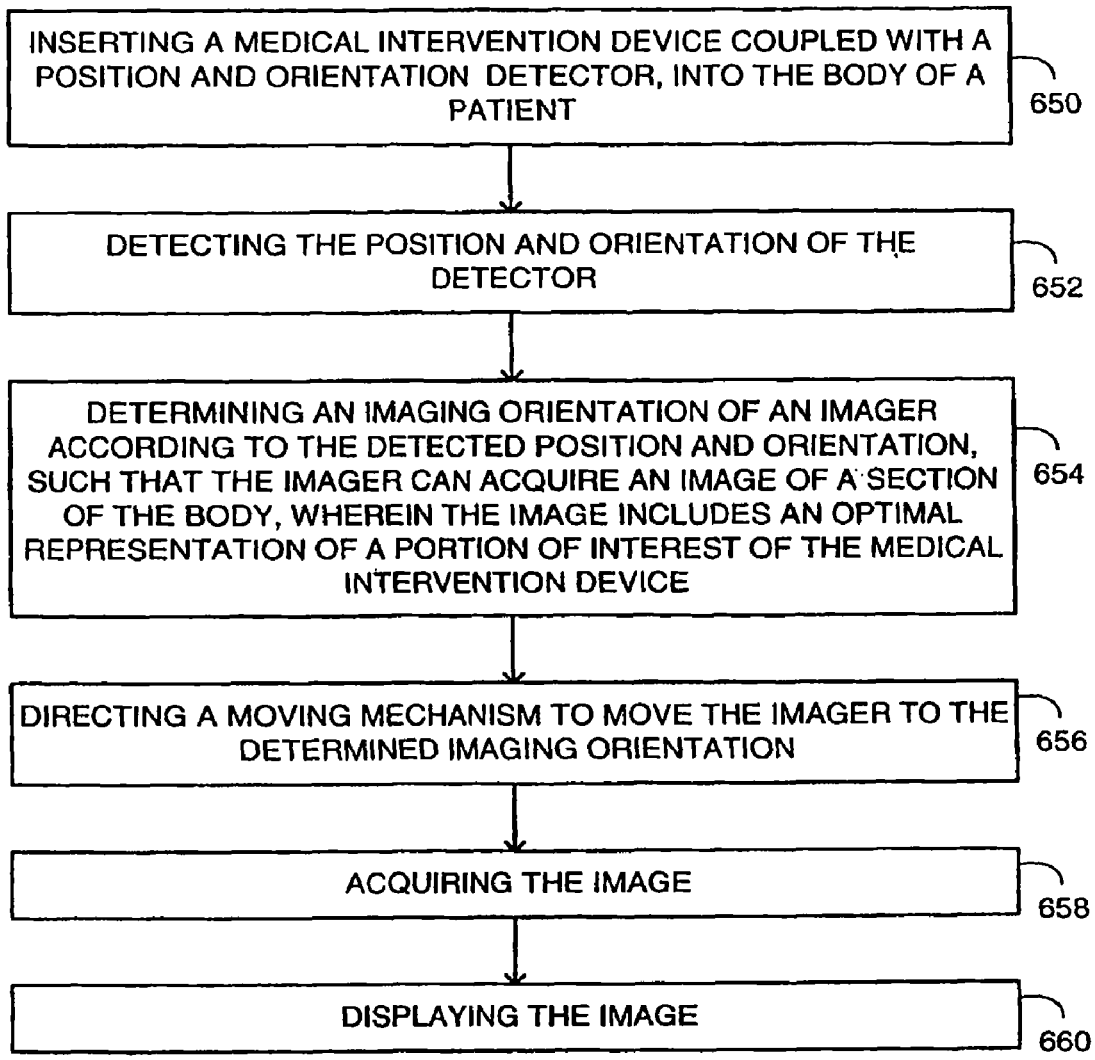
FIG. 12 is a schematic illustration of a method for operating the system of FIG. 11, operative according to another embodiment of the disclosed technique.

Reference is now made to FIG. 12, which is a schematic illustration of a method for operating the system of FIG. 11, operative according to another embodiment of the disclosed technique. In procedure 650, a medical intervention device coupled with a position and orientation detector, is inserted into the body of a patient. With reference to FIG. 11, device position and orientation detector 606 is located at a portion of interest (e.g., at distal end 628) of medical intervention device 604 and medical intervention device 604 is inserted into the body of patient 624. MPS 620, then detects the position and orientation of device position and orientation detector 606 and of imager position and orientation detector 608 (procedure 652). It is noted that the current position and orientation of imager 610 can be obtained internally, from sensors embedded in the imager, or externally, by attaching an MPS sensor to imager 610.

In procedure 654, an imaging orientation of an imager is determined according to the detected positions and orientations, such that the imager can acquire an image of a section of the body, wherein the image includes an optimal representation of a portion of interest of the medical intervention device. With reference to FIG. 11, processor 622 determines that the portion of interest of medical intervention device 604 (i.e., distal end 628), points along vector 622. Processor 622 further determines that imager 610 has to be moved to an orientation at which the radiation axis thereof points along vector 632.

At this orientation, imager 610 can radiate the body of patient 624 along an axis which is approximately perpendicular to the direction of distal end 628. Thus, at this orientation, imager 610 can acquire an image of a section of the body of patient 624, wherein the image includes an optimal representation of a portion of interest of medical intervention device 604.

Processor 622 provides a signal to moving mechanism 614 to move imager 610 to the orientation determined in procedure 654 (procedure 656). Imager 610 acquires the image (procedure 658) and provides a respective signal to a display to display the acquired image (procedure 660).

It will be appreciated by persons skilled in the art that the disclosed technique is not limited to what has been particularly shown and described hereinabove. Rather the scope of the disclosed technique is defined only by the claims, which follow.

The invention claimed is:

1. System for registering a first coordinate system with a second coordinate system relative to the body of a patient, the system comprising:
a first medical positioning system for detecting a first position and orientation of the body of a patient relative to a first coordinate system, said first medical positioning system being associated with and coupled with an imager, said imager acquiring at least one image from the body, said imager producing an image by associating said at least one image with said first position and orientation;
a second medical positioning system for detecting a second position and orientation of the body of a patient relative to a second coordinate system, said second medical positioning system is separate from said first medical positioning system, said second medical positioning system being associated with and coupled with a medical intervention device, said medical intervention device is different from said first imager, said second medical positioning system associating said device with said second position and orientation; and
a registering module coupled with said medical intervention device and with said second medical positioning system, said registering module registering said first coordinate system with said second coordinate system, according to said first position and orientation and said second position and orientation detected relative to the respective first and second coordinate systems.

2. The system according to claim 1, further comprising an image database coupled with said imager and with said registering module, wherein said imager stores said image in said image database, and wherein said registering module retrieves said image from said image database.

3. The system according to claim 1, further comprising a body position and orientation detector for coupling with the body of the patient, wherein said first medical positioning system detects said first position and orientation, when said body position and orientation detector is coupled with said first medical positioning system, and
wherein said second medical positioning system detects said second position and orientation, when said body position and orientation detector is coupled with said second medical positioning system.

4. The system according to claim 1, further comprising a device position and orientation detector coupled with said medical intervention device, wherein said second medical positioning system detects a device position and orientation of said medical intervention device via said device position and orientation detector,
wherein said registering module produces a representation of said medical intervention device, according to said device position and orientation.

5. The system according to claim 4, wherein said medical intervention device is selected from the group consisting of:
catheter;
drug delivery unit; and
tissue severing unit.

6. The system according to claim 1, wherein said imager is selected from the group consisting of:
fluoroscopy;
ultrasound;
thermography;
nuclear magnetic resonance; and
optical imaging.

7. The system according to claim 1, further comprising a display coupled with said registering module, for displaying at least said image.

8. The system according to claim 1, further comprising:
a processor coupled with said imager and with said registering module;
a first organ timing monitor coupled with said processor, said first organ timing monitor configured to detect a timing signal of an inspected organ of the body of the patient, when a first pulse sensor is coupled with said inspected organ and with said first organ timing monitor; and
a second organ timing monitor coupled with said registering module, said second organ timing monitor configured to detect said timing signal, when a second pulse sensor is coupled with said inspected organ and with said second organ timing monitor,
wherein said processor reconstructs said image by associating said at least one image with a respective one of said first position and orientation and with a respective time point of said timing signal, and
wherein said registering module registers said image with said medical intervention device, according to said respective first position and orientation, a respective one of said second position and orientation and said respective time point.

9. The system according to claim 8, further comprising an image database coupled with said processor and with said registering module, wherein said processor stores said image in said image database, and wherein said registering module retrieves said image from said image database.

10. The system according to claim 1, further comprising at least two body position and orientation detectors for coupling with the body of the patient and operative to alternately couple with said first medical positioning system and with said second medical positioning system, wherein said first medical positioning system detects said first position and orientation via said at least two body position and orientation detectors, when said at least two body position and orientation detectors are coupled with said first medical positioning system, wherein said second medical positioning system detects said second position and orientation via said at least two body position and orientation detectors, when said at least two body position and orientation detectors are coupled with said second medical positioning system, and wherein said registering module adjusts the scale of said first image and said second image, according to the difference between the distances between said at least two body position and orientation detectors, detected by each of said first medical positioning system and said second medical positioning system.

11. The system according to claim 1, further comprising a plurality of sensing units for coupling with the body of the patient and operative to alternately couple with said first medical positioning system and said second medical positioning system, wherein said first medical positioning system comprises:

a first transceiver to be coupled with said sensing units; and a first processor coupled with said first transceiver and with said imager, said first processor determining said first position and orientation according to a first signal received from said first transceiver, when said sensing units are coupled with said first transceiver; and wherein said second medical positioning system comprises:

a second transceiver to be coupled with said sensing units; and a second processor coupled with said second transceiver, said registering module and with said medical intervention device, said second processor determining said second position and orientation according to a second signal received from said second transceiver, when said sensing units are coupled with said second transceiver.

12. The system according to claim 11, wherein each of said sensing units comprises a location detector and an orientation detector.

13. The system according to claim 12, wherein said location detector is selected from the group consisting of:

electromagnetic coil; and sonar sensor.

14. The system according to claim 12, wherein said orientation detector is a gyroscope.

15. The system according to claim 11, further comprising:

a first sensing unit coupled with said first transceiver and with said first imager, said first processor determining an imager position and orientation of said imager according to a first signal received from said first transceiver; and a second sensing unit coupled with said second transceiver and with said medical intervention device, said second processor determining a medical intervention device position and orientation of said medical intervention device according to a second signal received from said second transceiver.

16. The system according to claim 11, wherein said second processor provides a position and orientation signal respective of said device position and orientation to said registering module, and wherein said registering module produces a representation of said medical intervention device, according to said position and orientation signal.

17. The system according to claim 1, further comprising a plurality of transmitters to be coupled with the body of the patient and operative to alternately couple with said first medical positioning system and said second medical positioning system, wherein said first medical positioning system comprises:

a first processor coupled with said imager;

a plurality of first receivers coupled with said first processor, wherein said second medical positioning system comprises:

a second processor coupled with said medical intervention device and with said registering module; and a plurality of second receivers coupled with said second processor, wherein said first processor determines said first position and orientation, when said first receivers receive wireless signals from said transmitters, and wherein said second processor determines said second position and orientation, when said second receivers receive wireless signals from said transmitters.

18. The system according to claim 17, wherein said first medical positioning system and said second medical positioning system determine said first position and orientation and said second position and orientation, respectively, by triangulation.

19. The system according to claim 1, wherein said interventional device comprises an image detector.

20. The system according to claim 19, wherein said registering module is further configured to register said first image with a second image produced according to a signal from said image detector.

* * * * *